(12) United States Patent
Wallace et al.

(10) Patent No.: US 11,109,873 B2
(45) Date of Patent: *Sep. 7, 2021

(54) PATELLA DRILL GUIDE AND TRIAL SURGICAL INSTRUMENT SYSTEM AND METHOD OF USING THE SAME

(71) Applicant: DEPUY IRELAND UNLIMITED COMPANY, County Cork (IE)

(72) Inventors: Matthew S. Wallace, Huntertown, IN (US); Jennifer B. Wyant, Warsaw, IN (US); Richard S. Jones, Shropshire (GB); David S. Barrett, Awbridge Hants (GB)

(73) Assignee: DEPUY IRELAND UNLIMITED COMPANY

( * ) Notice: Subject to any disclaimer, the term of this patent is extended or adjusted under 35 U.S.C. 154(b) by 325 days.

This patent is subject to a terminal disclaimer.

(21) Appl. No.: 16/149,895

(22) Filed: Oct. 2, 2018

(65) Prior Publication Data

US 2019/0029699 A1 Jan. 31, 2019

Related U.S. Application Data

(63) Continuation of application No. 13/630,924, filed on Sep. 28, 2012, now Pat. No. 10,085,758.

(51) Int. Cl.
*A61B 17/17* (2006.01)
*A61F 2/46* (2006.01)
*A61B 17/88* (2006.01)

(52) U.S. Cl.
CPC ...... *A61B 17/1767* (2013.01); *A61B 17/8866* (2013.01); *A61F 2/4684* (2013.01)

(58) Field of Classification Search
CPC ......... A61F 2002/0016; A61B 17/1677; A61B 17/1767

See application file for complete search history.

(56) References Cited

U.S. PATENT DOCUMENTS

| 2,181,746 A | 11/1939 | Siebrandt |
| 3,835,849 A | 9/1974 | McGuire |
| 4,191,861 A | 3/1980 | Walker |

(Continued)

FOREIGN PATENT DOCUMENTS

| EP | 791335 A1 | 8/1997 |
| EP | 992222 A2 | 4/2000 |

(Continued)

OTHER PUBLICATIONS

Depuy International, Ltd., PFC Sigma Rotating Platform Knee System With MBT Tray, Surgical Technique Brochure, 2003 (43 Pages), Cat. No. 9068-96-000, Depuy International, Ltd., Leeds, England.

(Continued)

*Primary Examiner* — Jerrah Edwards
*Assistant Examiner* — Christine L Nelson
(74) *Attorney, Agent, or Firm* — Barnes & Thornburg LLP

(57) ABSTRACT

An orthopaedic surgical instrument includes a patella trial and drill guide that may be used to both perform a surgical trial of the patellofemoral joint and guide the surgeon in drilling a number of anchor holes in the patella of the patient. A method of using such an orthopaedic surgical instrument is also disclosed.

10 Claims, 16 Drawing Sheets

(56) References Cited

U.S. PATENT DOCUMENTS

| | | |
|---|---|---|
| D260,927 S | 9/1981 | Glenn |
| D281,622 S | 12/1985 | Diamond |
| 4,565,192 A | 1/1986 | Shapiro |
| 4,633,862 A | 1/1987 | Petersen |
| 4,692,073 A | 9/1987 | Martindell |
| 5,002,547 A | 3/1991 | Poggie et al. |
| 5,021,055 A | 6/1991 | Burkinshaw et al. |
| 5,108,401 A | 4/1992 | Insall et al. |
| 5,116,338 A | 5/1992 | Poggie et al. |
| 5,129,907 A | 7/1992 | Heldreth et al. |
| 5,129,908 A | 7/1992 | Petersen |
| 5,147,365 A | 9/1992 | Whitlock et al. |
| 5,174,693 A | 12/1992 | Lee et al. |
| 5,222,955 A | 6/1993 | Mikhail |
| 5,250,050 A | 10/1993 | Poggie et al. |
| 5,258,032 A | 11/1993 | Bertin |
| 5,284,482 A | 2/1994 | Mikhail |
| 5,284,485 A | 2/1994 | Kammerer et al. |
| 5,312,409 A | 5/1994 | McLaughlin et al. |
| 5,382,254 A | 1/1995 | McGarry et al. |
| 5,415,663 A | 5/1995 | Luckman et al. |
| 5,470,328 A | 11/1995 | Furnish et al. |
| 5,484,451 A | 1/1996 | Akopov et al. |
| D367,531 S | 2/1996 | Price |
| 5,520,692 A | 5/1996 | Ferrante |
| 5,536,271 A | 7/1996 | Daly et al. |
| 5,542,947 A | 8/1996 | Treacy |
| D373,635 S | 9/1996 | Price |
| 5,575,793 A | 11/1996 | Carls et al. |
| 5,582,615 A | 12/1996 | Foshee et al. |
| 5,593,450 A | 1/1997 | Scott et al. |
| 5,611,802 A | 3/1997 | Samuelson et al. |
| 5,626,607 A | 5/1997 | Malecki et al. |
| 5,667,512 A | 9/1997 | Johnson |
| 5,716,361 A | 2/1998 | Masini |
| 5,716,362 A | 2/1998 | Treacy |
| 5,827,279 A | 10/1998 | Hughett et al. |
| 5,941,884 A | 8/1999 | Corvelli et al. |
| 5,944,723 A | 8/1999 | Colleran et al. |
| 5,957,926 A | 9/1999 | Masini |
| 5,968,051 A | 10/1999 | Luckman et al. |
| 6,010,509 A | 1/2000 | Delgado et al. |
| 6,056,754 A | 5/2000 | Haines et al. |
| 6,074,425 A | 6/2000 | Pappas |
| 6,080,162 A | 6/2000 | Dye et al. |
| 6,190,391 B1 | 2/2001 | Stubbs |
| 6,205,884 B1 | 3/2001 | Foley et al. |
| D459,474 S | 6/2002 | Bratt et al. |
| 6,419,675 B1 | 7/2002 | Gallo |
| D463,550 S | 9/2002 | Sherman |
| 6,551,316 B1 | 4/2003 | Rinner et al. |
| 6,589,248 B1 | 7/2003 | Hughes |
| 6,851,150 B2 | 2/2005 | Chiang |
| 6,855,150 B1 | 2/2005 | Linehan |
| 6,866,667 B2 | 3/2005 | Wood et al. |
| 6,905,514 B2 | 6/2005 | Carignan et al. |
| D549,331 S | 8/2007 | Tomatsu et al. |
| 7,344,540 B2 | 3/2008 | Smucker et al. |
| 7,356,902 B2 | 4/2008 | Snider et al. |
| 7,566,335 B1 | 7/2009 | Scott et al. |
| 7,632,279 B2 | 12/2009 | Bastian |
| 7,780,594 B2 | 8/2010 | Hutton |
| 7,806,899 B2 | 10/2010 | Hogg et al. |
| 7,878,989 B2 | 2/2011 | McMinn |
| 7,891,071 B2 | 2/2011 | Collazo |
| D634,011 S | 3/2011 | Phillips et al. |
| D638,541 S | 5/2011 | Claypool |
| 7,972,383 B2 | 7/2011 | Goldstein et al. |
| D642,678 S | 8/2011 | Dockstader et al. |
| D646,389 S | 10/2011 | Claypool et al. |
| 8,216,242 B2 | 7/2012 | Marchyn et al. |
| 8,834,574 B2 | 9/2014 | Todd et al. |
| 8,951,262 B2 | 2/2015 | Kecman et al. |
| 9,554,813 B2 | 1/2017 | Clever et al. |
| 9,700,330 B2 | 7/2017 | Wyant et al. |
| 9,855,065 B2 | 1/2018 | Wyant et al. |
| 10,085,758 B2 | 10/2018 | Wallace et al. |
| 2002/0115987 A1 | 8/2002 | Hildwein et al. |
| 2003/0163137 A1* | 8/2003 | Smucker ............ A61B 17/158 606/87 |
| 2004/0153066 A1 | 8/2004 | Coon et al. |
| 2004/0162561 A1* | 8/2004 | Marchyn ............ A61B 17/1677 606/78 |
| 2005/0240196 A1 | 10/2005 | Davis et al. |
| 2006/0058886 A1 | 3/2006 | Wozencroft |
| 2006/0142777 A1 | 6/2006 | Bastian |
| 2007/0118141 A1 | 5/2007 | Marchyn et al. |
| 2007/0150066 A1 | 6/2007 | McMinn |
| 2007/0162031 A1 | 7/2007 | Hogg et al. |
| 2007/0179626 A1 | 8/2007 | de la Barrera et al. |
| 2007/0233142 A1 | 10/2007 | Oliver |
| 2007/0260227 A1 | 11/2007 | Phan |
| 2008/0097450 A1 | 4/2008 | Brown et al. |
| 2008/0114366 A1 | 5/2008 | Smucker et al. |
| 2008/0177394 A1 | 7/2008 | Chauhan |
| 2008/0221569 A1 | 9/2008 | Moore et al. |
| 2008/0228190 A1 | 9/2008 | Sherry et al. |
| 2008/0306484 A1 | 12/2008 | Coon et al. |
| 2009/0088753 A1 | 4/2009 | Aram et al. |
| 2009/0264737 A1 | 10/2009 | Haechler et al. |
| 2009/0326661 A1 | 12/2009 | Wright et al. |
| 2010/0030223 A1 | 2/2010 | Keller |
| 2010/0121389 A1 | 5/2010 | Librot et al. |
| 2010/0152742 A1 | 6/2010 | Nevels et al. |
| 2010/0160924 A1 | 6/2010 | Soliman |
| 2010/0168753 A1 | 7/2010 | Edwards et al. |
| 2010/0204701 A1 | 8/2010 | Tallarida et al. |
| 2011/0066193 A1 | 3/2011 | Lang et al. |
| 2012/0078261 A1 | 3/2012 | Kecman et al. |
| 2012/0179264 A1 | 7/2012 | Todd et al. |
| 2013/0023883 A1 | 1/2013 | Wright et al. |
| 2013/0023890 A1 | 1/2013 | Kecman et al. |
| 2013/0030443 A1 | 1/2013 | Wright et al. |
| 2013/0030539 A1 | 1/2013 | Wright et al. |
| 2013/0035693 A1 | 2/2013 | Wright et al. |
| 2013/0079787 A1 | 3/2013 | Spencer Jones et al. |
| 2013/0079788 A1 | 3/2013 | Spencer Jones et al. |
| 2013/0079789 A1 | 3/2013 | Randle et al. |
| 2013/0211410 A1 | 8/2013 | Landes et al. |
| 2014/0094818 A1 | 4/2014 | Wallace et al. |

FOREIGN PATENT DOCUMENTS

| | | |
|---|---|---|
| EP | 1723916 A1 | 11/2006 |
| EP | 1967143 A2 | 9/2008 |
| EP | 2574314 A1 | 4/2013 |
| FR | 2737848 A1 | 2/1997 |
| GB | 2433695 A | 7/2007 |
| WO | 9945856 A1 | 9/1999 |
| WO | 2005110249 A1 | 11/2005 |
| WO | 2008112996 A1 | 9/2008 |
| WO | 2013003730 A1 | 1/2013 |

OTHER PUBLICATIONS

Depuy Orthopaedics, Inc., Sigma High Performance Instruments, Design Rationale, 2007 (12 Pages), Pub. No. 0612-54-506 (Rev. 2), Depuy Orthopaedics, Inc., Warsaw, IN.

Depuy Orthopaedics, Inc., LCS High Performance Instruments, Surgical Technique Guide, 2008, (44 Pages), Pub. No. 0612-85-506, Depuy Orthopaedics, Inc., Warsaw, IN.

Depuy Orthopaedics, Inc. Sigma High Performance Instruments, Classic Surgical Technique, 2010, (52 Pages), Pub. No. 0612-89-510, Depuy Orthopaedics, Inc., Warsaw, IN.

European Search Report, European Pat. App. No. 11175824.9-2310, dated Dec. 16, 2011 (7 Pages).

European Search Report for European Application No. 12174682.0-2310, dated Sep. 5, 2012, 6 pages.

European Search Report for European Application No. 12174683.8-2310, dated Sep. 3, 2012, 6 pages.

European Search Report for European Application No. 12186675.0-2310, dated Dec. 12, 2012, 7 pages.

(56) References Cited

OTHER PUBLICATIONS

European Search Report for European Application No. 12186700.6-2310, dated Dec. 13, 2012, 8 pages.
European Search Report for European Application No. 12186728.7-2310, dated Dec. 14, 2012, 8 pages.
International Search Report, International Application No. PCT/US12/44947, dated Oct. 12, 2012, 3 pages.
European Search Report for European Application No. 13186416.7-1654, dated Dec. 6, 2013, 7 pages.
European Search Report, European Pat. App. No. 12191753.8-2310, dated Jan. 3, 2013 (6 Pages).
European Search Report for European Application No. 13186401.9-1654, dated Jan. 17, 2014, 7 pages.
Extended European Search Report, European Application No. 16160477.2-1654, dated May 11, 2016, 8 pages.

* cited by examiner

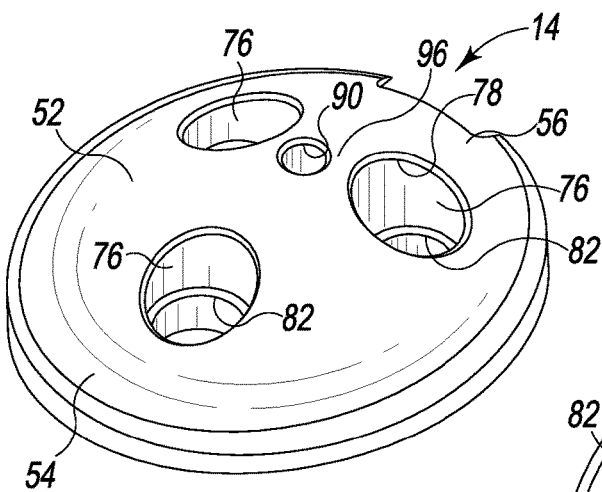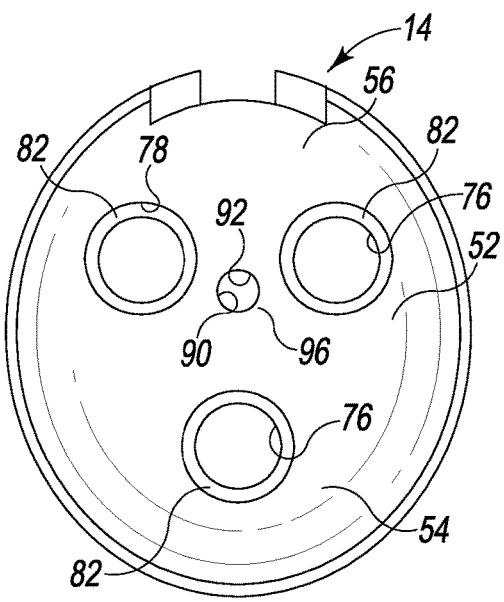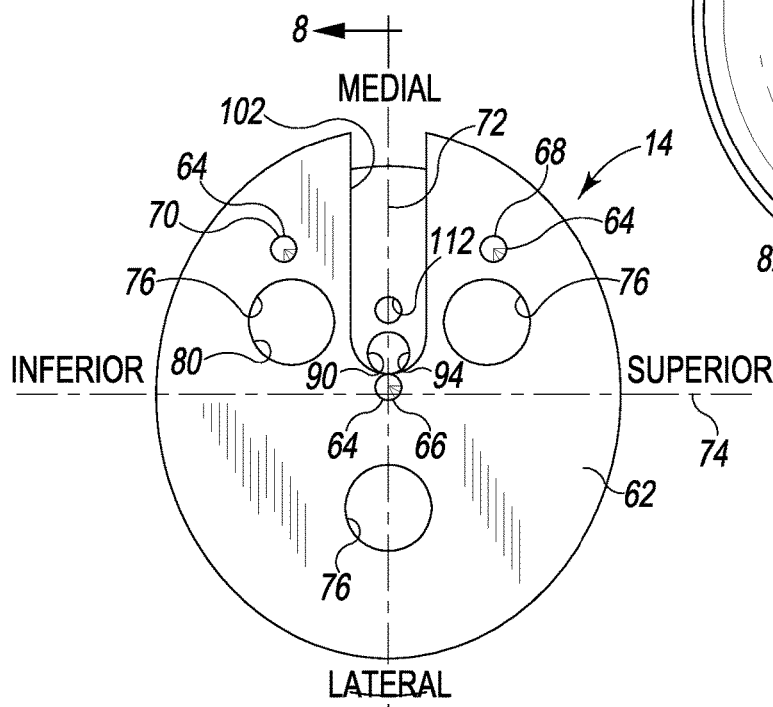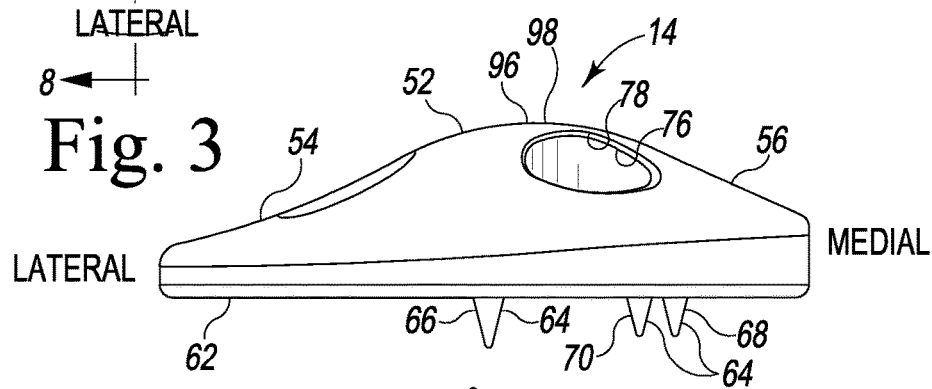

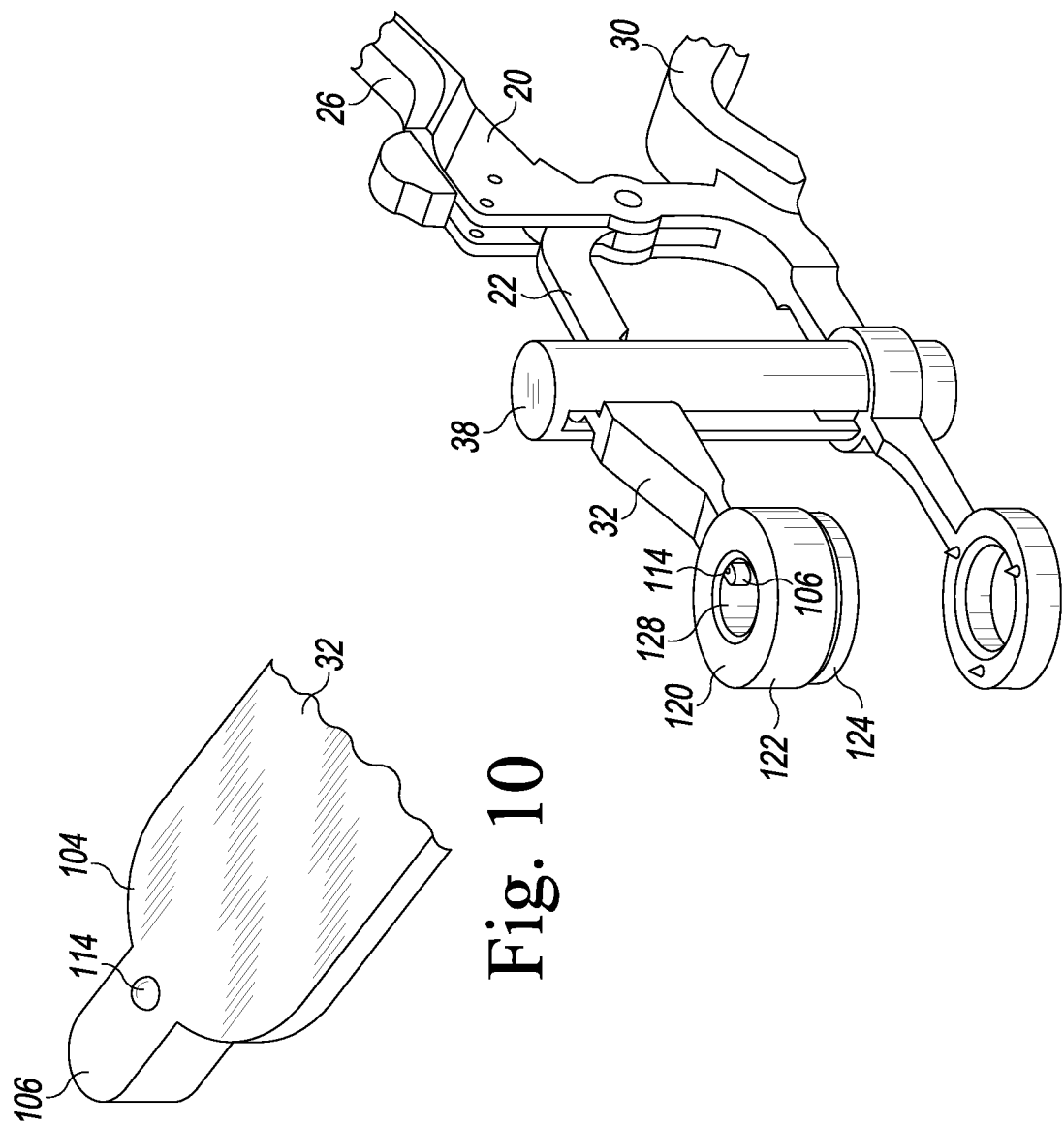
Fig. 10
Fig. 12
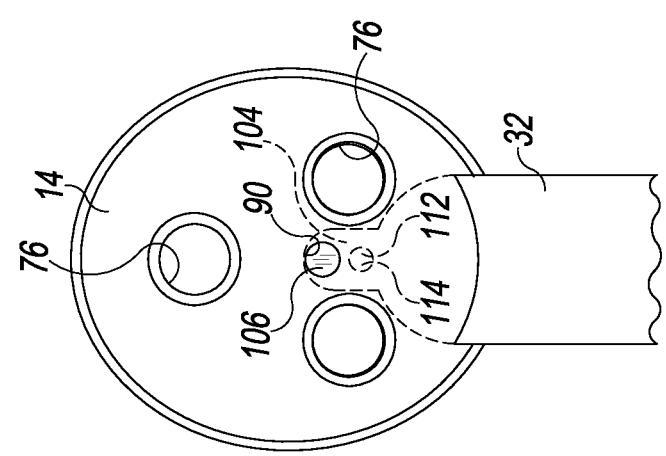
Fig. 11

US 11,109,873 B2

PATELLA DRILL GUIDE AND TRIAL SURGICAL INSTRUMENT SYSTEM AND METHOD OF USING THE SAME

This application is a continuation application of U.S. patent application Ser. No. 13/630,924, now U.S. Pat. No. 10,085,758, which is expressly incorporated herein by reference.

CROSS REFERENCE

Cross reference is made to each of U.S. patent application Ser. No. 13/630,935, now U.S. Pat. No. 9,855,065, entitled "ORTHOPAEDIC SURGICAL INSTRUMENT ASSEMBLY FOR IMPLANTING A PROSTHETIC PATELLA COMPONENT" by Jennifer B. Clever et al.; U.S. patent application Ser. No. 13/630,951, now U.S. Pat. No. 9,554,813, entitled "PATELLA DRILL GUIDE AND TRIAL SURGICAL INSTRUMENT" by Jennifer B. Clever et al.; and U.S. patent application Ser. No. 13/630,965, now U.S. Pat. No. 9,700,330, entitled "METHOD FOR SURGICALLY IMPLANTING A PROSTHETIC PATELLA COMPONENT" by Jennifer B. Clever et al. Each of these applications, now patents, is assigned to the same assignee as the present application and hereby incorporated by reference.

TECHNICAL FIELD

The present disclosure relates generally to orthopaedic surgical instruments and, more particularly, to patella surgical instruments.

BACKGROUND

Joint arthroplasty is a well-known surgical procedure by which a diseased and/or damaged natural joint is replaced by a prosthetic joint. A typical knee prosthesis includes a tibial tray, a femoral component, and a polymer insert or bearing positioned between the tibial tray and the femoral component. In some cases, the knee prosthesis may also include a prosthetic patella component, which is secured to a posterior side of the patient's surgically-prepared patella. To secure the prosthetic component to the patella, an orthopaedic surgeon may resect the posterior side of the patient's natural patella to prepare the natural patella to receive the prosthetic component. In use, the patella prosthetic component articulates with the femoral component during extension and flexion of the patient's knee.

SUMMARY

According to one aspect, a patella drill guide and trial instrument includes a posterior trial bearing surface configured to articulate with a condylar surface of a prosthetic femoral component. The posterior trial bearing surface has a curved peak surface that defines the posterior-most surface of the patella drill guide and trial instrument. The patella drill guide and trial instrument also includes an anterior surface having a number of spikes extending outwardly therefrom and a number of drill guide holes extending through the patella drill guide and trial instrument from the posterior trial bearing surface to the anterior surface. The patella drill guide and trial instrument also includes an alignment bore extending through the patella drill guide and trial instrument from the posterior trial bearing surface to the anterior surface.

In an embodiment, the alignment bore has a different diameter than the number of drill guide holes. In a specific embodiment, the alignment bore has a smaller diameter than the number of drill guide holes.

A tip of the curved peak surface may define the posterior-most point of the patella drill guide and trial instrument, with the alignment bore being formed in the tip of the curved peak surface.

The number of drill guide holes may be embodied as counterbored holes.

According to another aspect, a patella drill guide and trial instrument includes a posterior trial bearing surface configured to articulate with a condylar surface of a prosthetic femoral component. The posterior trial bearing surface includes a curved peak surface having a tip that defines the posterior-most point of the patella drill guide and trial instrument. The patella drill guide and trial instrument may also include an anterior surface having a number of spikes extending outwardly therefrom, and a number of drill guide holes extending through the patella drill guide and trial instrument from the posterior trial bearing surface to the anterior surface. The patella drill guide and trial instrument may further include an alignment bore formed in the tip of the curved peak surface and extending through the patella drill guide and trial instrument to the anterior surface.

In an embodiment, the alignment bore has a different diameter than the number of drill guide holes. In a specific embodiment, the alignment bore has a smaller diameter than the number of drill guide holes.

The number of drill guide holes may be embodied as counterbored holes.

According to yet another aspect, a method of performing an orthopaedic surgical procedure on a patella of a patient includes forming a hole in the apex of the patella of the patient and resecting the patella of the patient to produce a generally planar resected patellar surface after the hole is formed in the apex of the patella of the patient. A drill guide, having an alignment bore formed therein, may then be positioned on the resected patellar surface such that the alignment bore of the drill guide is aligned with the hole formed in the patella of the patient.

The hole may be formed in the apex of the patella of the patient by drilling the hole in the apex of the patella of the patient.

A drill may be advanced through a number of guide holes formed in the drill guide and into the resected patellar surface so as to drill a number of anchor holes in the patella of the patient. The drill guide may then be removed from the resected patellar surface, and a number of anchor pegs of a patella component inserted into the anchor holes.

The drill guide may be positioned on the resected patellar surface by visualizing the hole formed in the patella of the patient through the alignment bore, and aligning the drill guide such that the alignment bore aligns with the hole formed in the patella of the patient.

The hole formed in the patella of the patient may be drilled in the patella of the patient to a predetermined depth, and the thickness of patellar bone that is resected is less than the predetermined depth such that the drilled hole is visible on the resected patellar surface.

The patellofemoral joint may be trialed with the drill guide positioned on the patella of the patient, and the a drill may be advanced through a number of guide holes formed in the drill guide and into the resected patellar surface so as to drill a number of anchor holes in the patella of the patient subsequent to trialing the patellofemoral joint.

BRIEF DESCRIPTION OF THE DRAWINGS

The detailed description particularly refers to the following figures, in which:

FIG. 2 is an enlarged perspective view of the patella drill guide and trial instrument of the orthopaedic surgical instrument assembly of FIG. 1;

FIG. 3 is a bottom elevation view of the patella drill guide and trial instrument of FIG. 2;

FIG. 4 is a top elevation view of the patella drill guide and trial instrument of FIG. 2;

FIG. 5 is a side elevation view of the patella drill guide and trial instrument of FIG. 2;

FIG. 10 is an enlarged fragmentary perspective view of the connector of the removable clamp of the orthopaedic surgical instrument assembly of FIG. 1;

FIG. 11 is a fragmentary top elevation view showing the patella drill guide and trial instrument secured to the removable clamp;

FIG. 12 is a fragmentary perspective view showing the compression socket secured to the removable clamp;

DETAILED DESCRIPTION OF THE DRAWINGS

Figure 1:
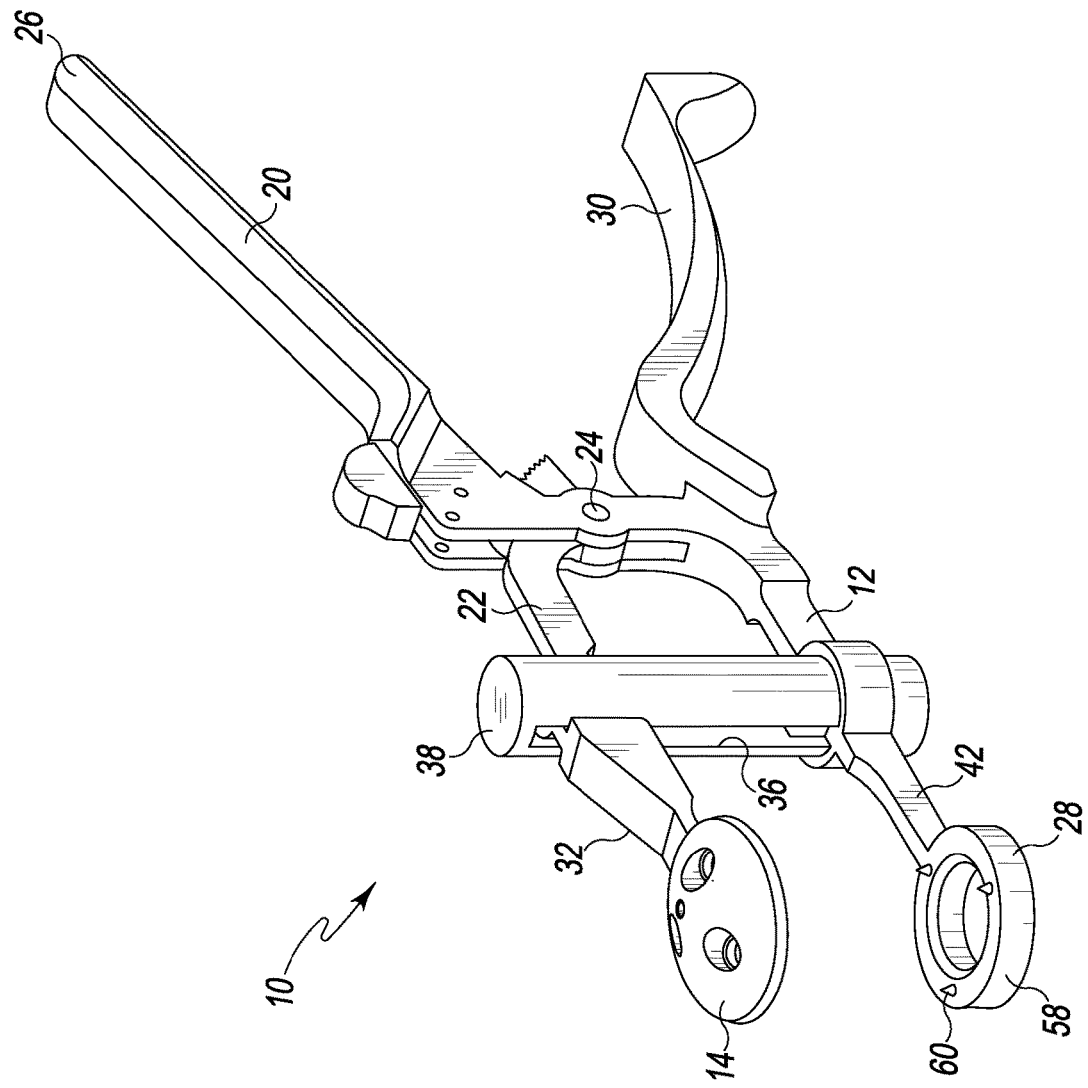
FIG. 1 is a perspective view of an orthopaedic surgical instrument assembly showing the patella drill guide and trial instrument secured to the removable clamp.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Figure 18:
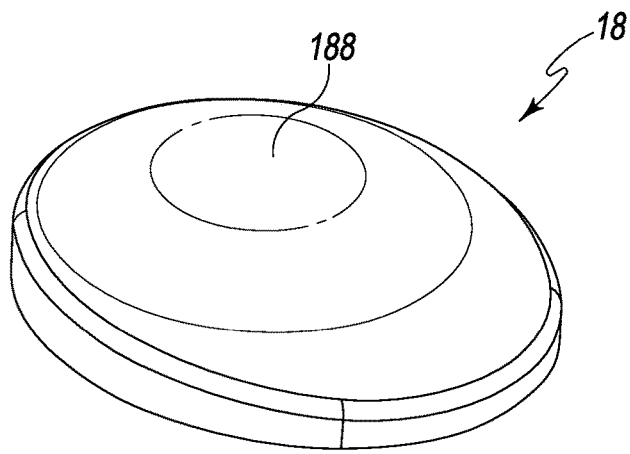
FIG. 18 is a top perspective view of a modified dome patella component that may be implanted with the instruments and methods described herein.

Referring to FIG. 1, an orthopaedic surgical instrument assembly 10 includes a removable patella clamp 12 and a patella drill guide and trial instrument 14 configured to be secured to the patella clamp 12. As described in greater detail below, the instrument assembly 10 is utilized to surgically prepare a patient's patella 16 for implantation of a prosthetic patella component 18 (see FIGS. 18 and 19). To do so, the patella drill guide and trial instrument 14 may be used as both a trial instrument to trial the patellofemoral joint and as a drill guide to drill anchor holes into the planar, resected posterior surface of the patient's patella 16. The surgeon may also use the patella drill guide and trial instrument 14 to size and select a patella prosthetic component suitable for use with the particular patient's patella.

Figure 9:
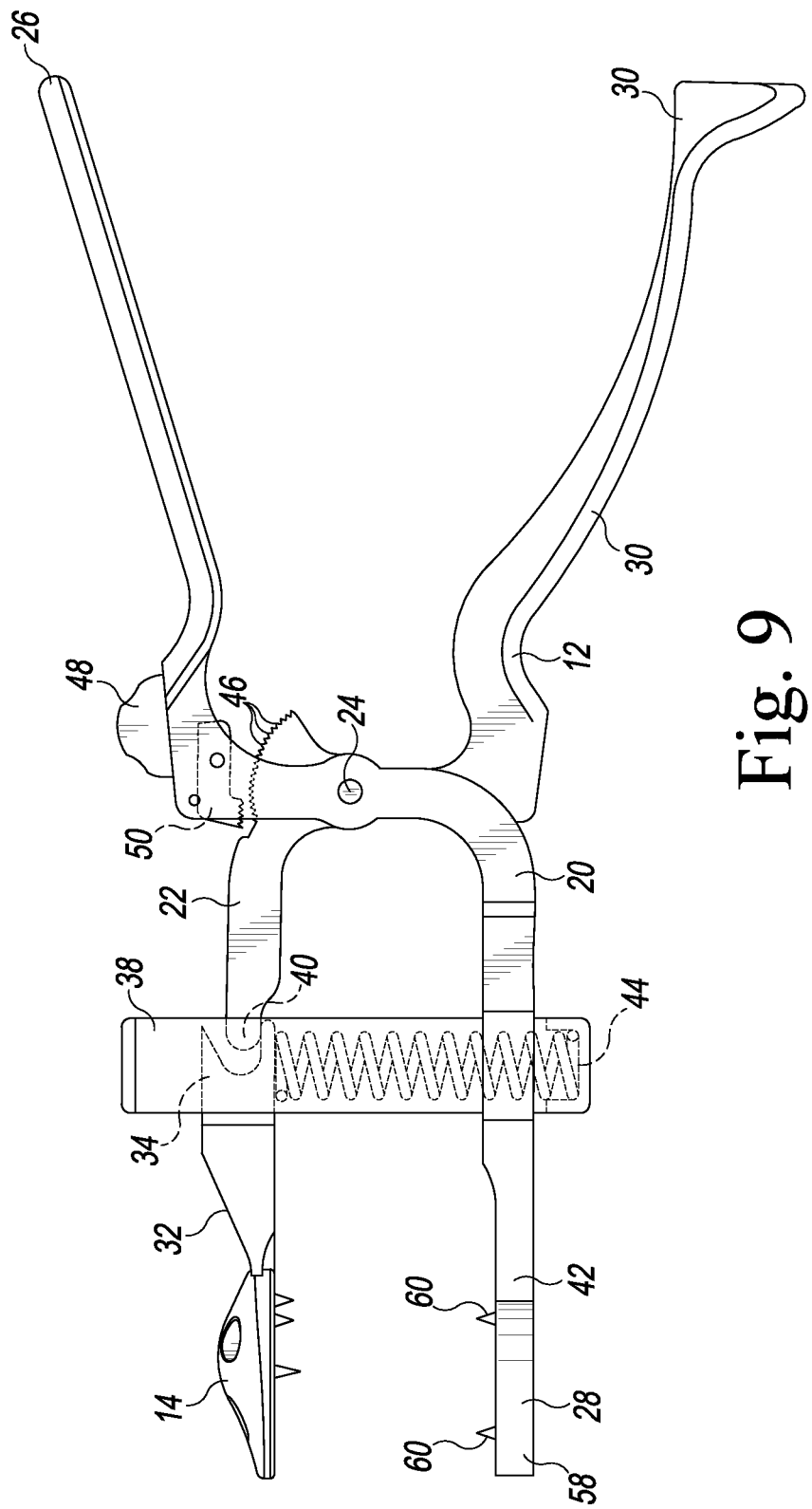
FIG. 9 is a side elevation view of the orthopaedic surgical instrument assembly of FIG. 1.

As shown in FIG. 1, the patella clamp 12 of the instrument assembly 10 includes a pair of levers 20, 22 pivoted together with a pivot pin 24. The proximal end of the lever 20 includes an upper handle 26, with the distal end of the lever 20 having a retaining socket 28. The proximal end of the lever 22 includes a lower handle 30, with the distal end of the lever 22 having a connector 32 (see FIG. 10). The lever 22 is modular in design in that the connector 32 is not integrally formed with the lower handle 30. A proximal end 34 of the connector 32 is captured in a slot 36 formed in a cylinder housing 38. As shown in FIG. 9, the proximal end 34 of the connector 32 is coupled to the distal end 40 of the lower handle 30 within the cylinder housing 38 such that the connector 32 is maintained in substantially parallel relationship with the distal end 42 of the lever 20 as it translates upwardly and downwardly within the cylinder housing 38. A compression spring 44 (see FIG. 9) is positioned in the cylinder housing 38 and exerts a spring bias on the proximal end 34 of the connector 32 so as to urge the connector 32 in a direction away from the retaining socket 28.

When a surgeon squeezes or otherwise urges the two handles 26, 30 toward one another, the levers 20, 22 pivot about the pin 24 thereby causing the connector 32 and the retaining socket 28 to move toward one another. When the surgeon releases the two handles 26, 30, the spring bias of the compression spring 44 urges the connector 32 away from the retaining socket 28 thereby causing the levers 20, 22 to pivot about the pin 24 so as to move the two handles 26, 30 away from one another.

As can be seen in FIG. 9, the lever 22 has a number of ratchet teeth 46 formed therein. A button 48 is secured to the lever 20 near its upper handle 26. The button 48 engages a locking pawl 50 such that the locking pawl 50 is moved into engagement with the ratchet teeth 46 by sliding the button 48 in a direction toward the cylinder housing 38, and disengaged from the ratchet teeth 46 by sliding it in the opposite direction. When the locking pawl 50 engages ratchet teeth 46, the levers 20, 22 of the patella clamp 12 are locked and therefore prevented from moving relative to one another. When the locking pawl 50 is disengaged from the ratchet teeth 46, the levers 20, 22 of the patella clamp 12 are free to move relative to one another.

As can be seen in FIG. 1, in the illustrative embodiment described herein, the clamp's retaining socket 28 is embodied as a ring 58 having a number of spikes 60 extending outwardly therefrom. The spikes 60 face toward a number of spikes of the patella drill guide and trial instrument 14 when the instrument 14 is secured to the clamp 12. In such an arrangement the clamp's spikes 60 cooperate with the spikes of the patella drill guide and trial instrument 14 to capture the patella 16 therebetween.

The patella clamp 12 may be constructed from a medical-grade metal such as stainless steel, cobalt chrome, or titanium, although other metals or alloys may be used.

Referring now to FIGS. 2-8, the patella drill guide and trial instrument 14 is shown in greater detail. As alluded to above, the patella drill guide and trial instrument 14 is used for fit assessment during a surgical procedure to implant the prosthetic patella component 18 into a patient's surgically-prepared patella 16. In essence, the patella drill guide and trial instrument 14 is used to ensure proper size selection of the ultimate patella component 18 (i.e., the patella component 18 that is ultimately implanted in the patient's patella 16). As will be discussed below in greater detail, the patella drill guide and trial instrument 14 also functions as a drill guide for guiding a drill bit used to drill the anchor holes in the patient's surgically-prepared patella 16 to receive the anchor pegs of the patella component 18 (see FIG. 30).

Figure 28:
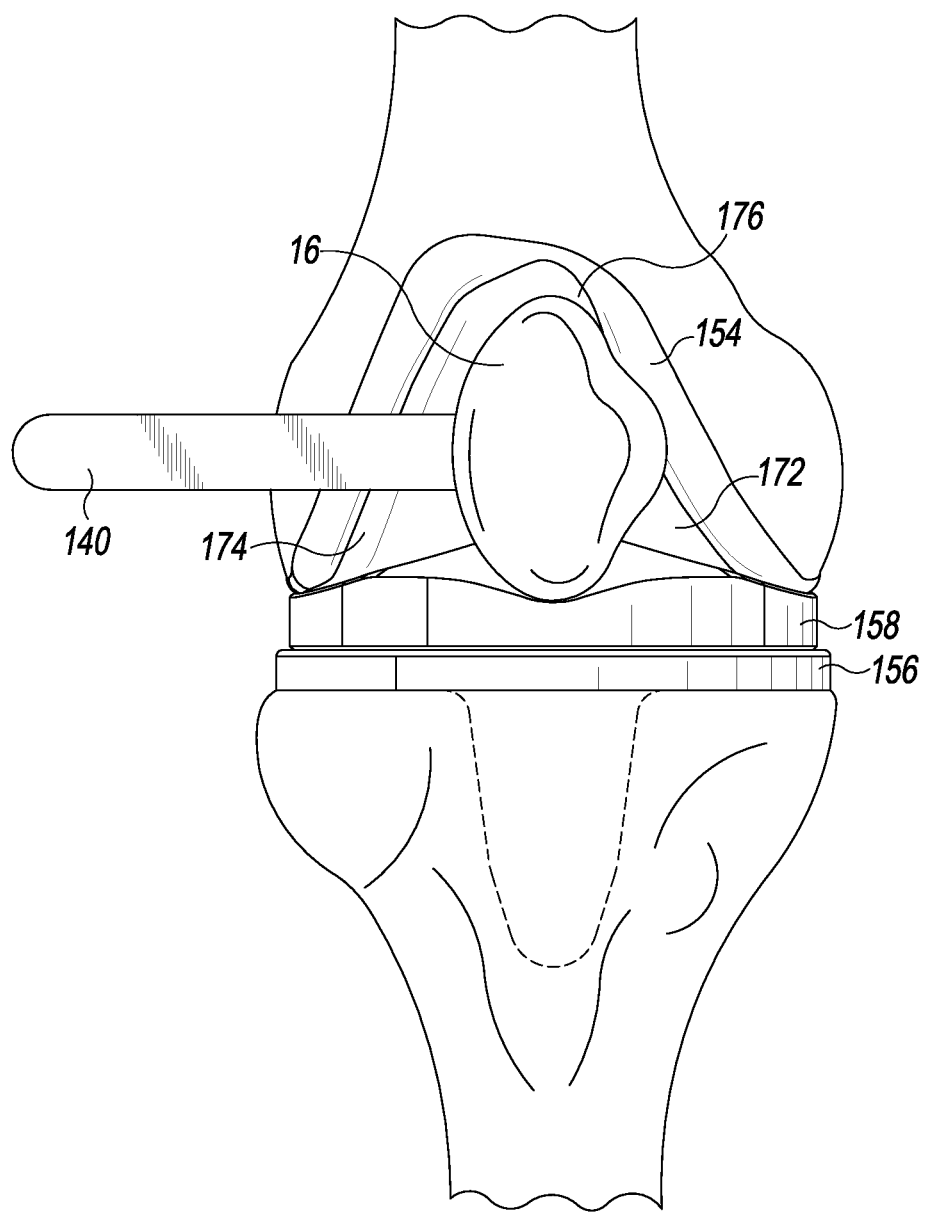
FIGS. 28 and 29 are surgical views showing the alignment handle being used to assess rotational positioning of the patella drill guide and trial instrument 14 during trialing of the patellafemoral joint.
Figure 29:
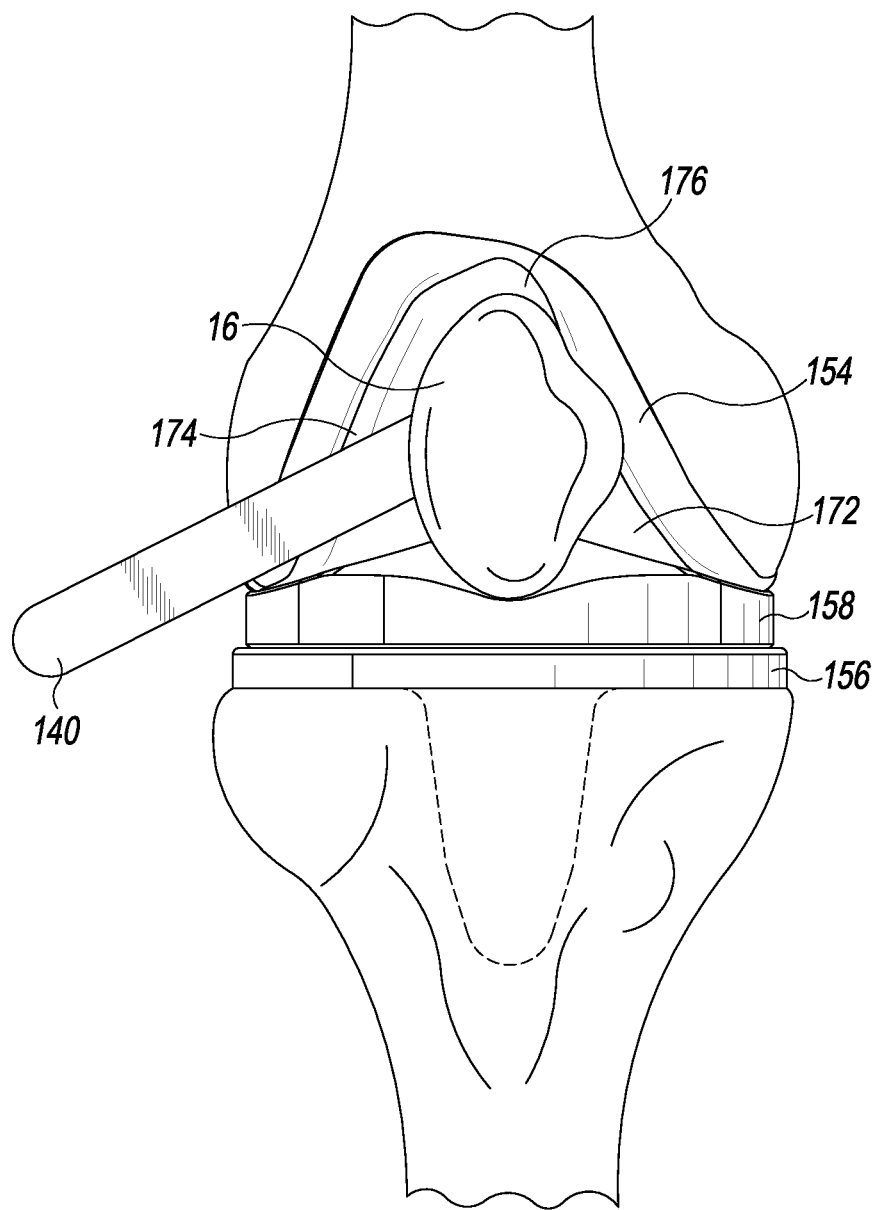

As shown in FIGS. 2, 5, 7, and 8, the patella drill guide and trial instrument 14 includes a posterior trial bearing surface 52 in the form of a curved peak surface configured to articulate with the condylar surface of the a prosthetic femoral component 154 (see FIGS. 28 and 29). In particular, the posterior trial bearing surface 52 of the patella drill guide and trial instrument 14 includes a lateral trial articular surface 54 and a medial trial articular surface 56. The trial articular surfaces 54, 56 are configured to articulate with a lateral condyle surface 172 and a medial condyle surface 174, respectively, of the femoral component 154. The femoral component 154 is configured to emulate the configuration of the patient's natural femoral condyles, and, as such, the lateral condyle surface 172 and the medial condyle surface 174 are configured (e.g., curved) in a manner which mimics the condyles of the natural femur. The lateral condyle surface 172 and the medial condyle surface 174 are spaced apart from one another thereby defining trochlear groove 176 therebetween.

As can be seen in FIGS. 3, 5, 7, and 8, the patella drill guide and trial instrument 14 also includes a flat anterior surface 62 having a number of fixation members, such as spikes 64, extending anteriorly away therefrom. The spikes 64 are configured to be inserted into a surgically prepared posterior surface of the patient's natural patella (not shown). In such a way, the posterior trial bearing surface 52 of the patella drill guide and trial instrument 14 faces toward the femoral component 154 thereby allowing the posterior trial bearing surface 52 to articulate with the femoral condyle surfaces 172, 174 during flexion and extension of the patient's knee during a patellofemoral trialing procedure.

As shown in FIGS. 3, 5, 7, and 8, in the exemplary embodiment described herein, the spikes 64 of the patella drill guide and trial instrument 14 include a center spike 66 that is centered in the superior/inferior direction. This is shown geometrically in FIG. 3 where an imaginary line 72 bisects the anterior surface 62 of the patella drill guide and trial instrument 14 in the superior/inferior direction. As can be seen, the center of the center spike 66 is located on the imaginary line 72 thereby centering the center spike 66 in the superior/inferior direction. The spikes 64 of the patella drill guide and trial instrument 14 also include a pair of peripheral spikes 68, 70. As can be seen in FIG. 3, the center of the peripheral spike 68 is located on the superior half of the anterior surface 62 of the patella drill guide and trial instrument 14 (i.e., it is located superiorly of the imaginary line 72), with the other peripheral spike 70 being located on the inferior half of the anterior surface 62 of the patella drill guide and trial instrument 14 (i.e., it is located inferiorly of the imaginary line 72).

As can be seen in FIG. 3, in the exemplary embodiment described herein, each of the spikes 64 is medially located on the anterior surface 62 of the patella drill guide and trial instrument 14. In particular, the respective centers of each of the center spike 66 and the peripheral spikes 68, 70 are located on the medial half of the anterior surface 62 of the patella drill guide and trial instrument 14. This is shown geometrically in FIG. 3 where an imaginary line 74 bisects the anterior surface 62 of the patella drill guide and trial instrument 14 in the medial/lateral direction. The centers of each of the center spike 66 and a pair of peripheral spikes 68, 70 is positioned medially of the imaginary line 74 (i.e., positioned between the imaginary line 74 and the medial-most edge of the patella drill guide and trial instrument 14). Such medial positioning of the spikes 64 allows for fixation to the less sclerotic (i.e., softer) bone tissue generally present on the medial side of the patella 16.

Figure 7:
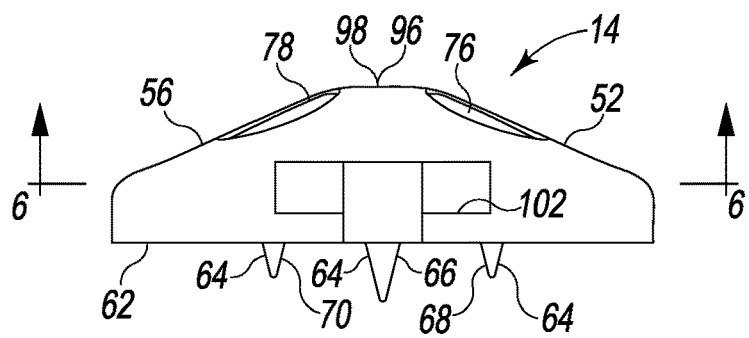
FIG. 7 is a side elevation view of the patella drill guide and trial instrument showing the instrument's connector.
Figure 8:
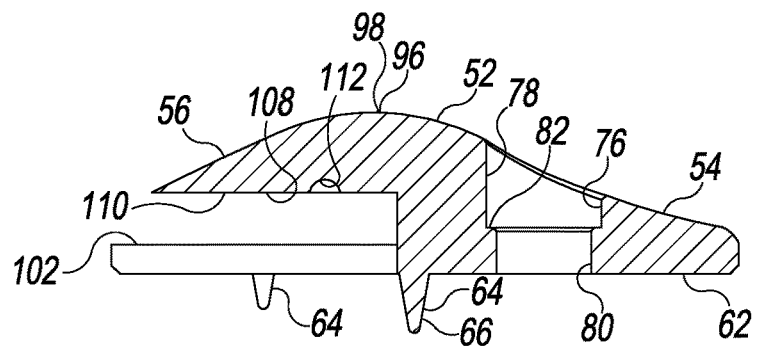
FIG. 8 is a cross section view of the patella drill guide and trial instrument taken along the line 8-8 of FIG. 3, as viewed in the direction of the arrows.

As can be seen in FIGS. 5, 7, and 8, the center spike 66 is longer than both the peripheral spikes 68, 70. In such a way, rotational positioning of the patella drill guide and trial instrument 14 can be achieve prior to securing it in its final position on the resected posterior surface of the patient's patella 16. In particular, as will be described in more detail below, the surgeon may first insert the tip of the center spike 66 into the resected posterior surface of the patient's patella 16 and then alter the rotational position of the patella drill guide and trial instrument 14 by rotating it relative to the resected posterior surface of the patient's patella 16 about its central axis defined by the center spike 66. Once the patella drill guide and trial instrument 14 has been rotated into a desired alignment position, the instrument 14 may be pressed into the resected posterior surface of the patient's patella 16 such that the peripheral spikes 68, 70 engage the bone tissue of the resected patella surface thereby preventing further rotation and maintaining the patella drill guide and trial instrument 14 in its desired rotational position relative to the resected posterior surface of the patient's patella 16.

The patella drill guide and trial instrument's body has a number of drill guide holes 76 formed therein. The drill guide holes 76 extend throughout the entire thickness of the patella drill guide and trial instrument's body. That is, a posterior end 78 of the drill guide holes 76 opens into the posterior trial bearing surface 52 of the patella drill guide and trial instrument 14, with the opposite anterior end 80 of the drill guide holes 76 opening into the instrument's anterior surface 62. The guide holes 76 function as drill guides for guiding a drill bit 84 used to drill the anchor holes 180 in the patient's surgically-prepared patella 16 to receive the anchor pegs of the patella component 18 (see FIGS. 30 and 31). As such, the size and position of each of the drill guide holes 76 coincides with the size and position of the anchor pegs 182 of the patella component 18 (see FIG. 19).

Figure 30:
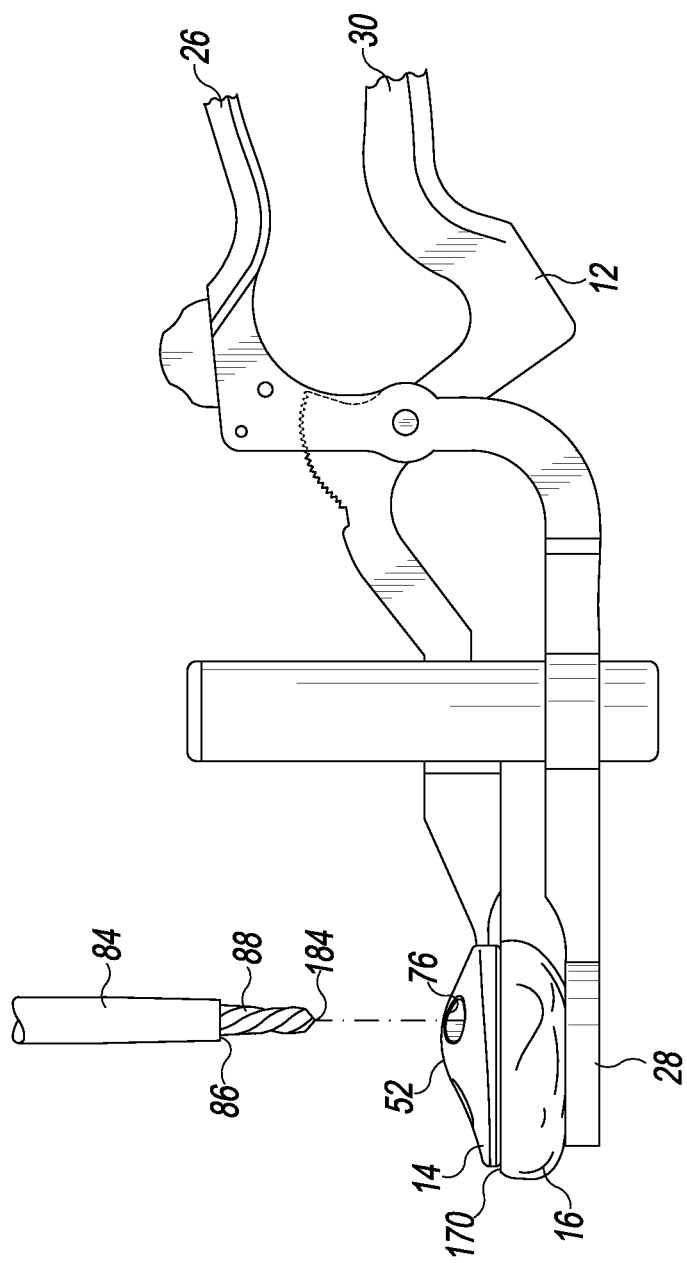
FIG. 30 is a surgical view showing the anchor holes being drilled in the patient's patella through the guide holes of the patella drill guide and trial instrument 14.

As can be seen best in FIGS. 2, 4, and 8, in the exemplary embodiment described herein, each of the drill guide holes 76 is counterbored. As such, the drill guide holes 76 have a larger diameter at their posterior ends 78 than they do at their anterior ends 80 thereby defining a shoulder 82 therebetween. The shoulder 82 functions as a depth stop to ensure the surgical drill bit 84 used to drill the anchor holes 182 in the patient's patella 16 drills to the desired depth. In particular, as can be seen in FIG. 30, the surgical drill bit 84 used to drill the anchor holes in the patient's patella 16 includes an annular collar 86 positioned above the upper end of the bit's cutting flutes 88. During use, the drill bit 84 may be advanced through one of the drill guide holes 76 and into the bone tissue of the patient's patella 16 until the lower surface of the collar 86 bottoms out or otherwise engages the shoulder 82 of the counterbored guide hole 76.

As shown best in FIGS. 1-3, the patella drill guide and trial instrument 14 has an alignment bore 90 formed therein. Like the drill guide holes 76, the alignment bore 90 extends throughout the entire thickness of the patella drill guide and trial instrument's body. That is, a posterior end 92 of the alignment bore 90 opens into the posterior trial bearing surface 52 of the patella drill guide and trial instrument 14, with the opposite anterior end 94 of the alignment bore 90 opening into a slot 102 of the instrument's connector.

The alignment bore 90 functions as a visual alignment guide that allows the surgeon to align the apex of the patella drill guide and trial instrument 14 with the former location of the apex of the patient's natural patella 16 prior to resection of the patella 16. In particular, a tip 96 of the curved peak surface of the posterior trial surface 52 defines the posterior-most point 98 of the patella drill guide and trial instrument 14. The alignment bore is formed in (i.e., opens into) the tip 96 of the posterior trial surface 52. As will be described below in greater detail, a surgeon may form (e.g., drill) a hole in the apex of the patient's natural patella 16 before resecting it. The hole is drilled to a depth that is deeper than the thickness of the bone to be removed during patella resection. As such, a shallow hole or indentation is still visible in the planar surgically-resected patella surface subsequent to bone removal. The surgeon may align the alignment bore 90 with this remaining hole in the patellar bone to align the apex of the patella drill guide and trial instrument 14 with the former location of the apex of the patient's natural patella 16.

As can be seen in FIGS. 2-4 and 6, the alignment bore 90 has a diameter that is smaller than the diameter of each of the drill guide holes 76. In such a way, the surgical drill bit 84 cannot inadvertently be passed through the alignment bore 90.

Figure 6:
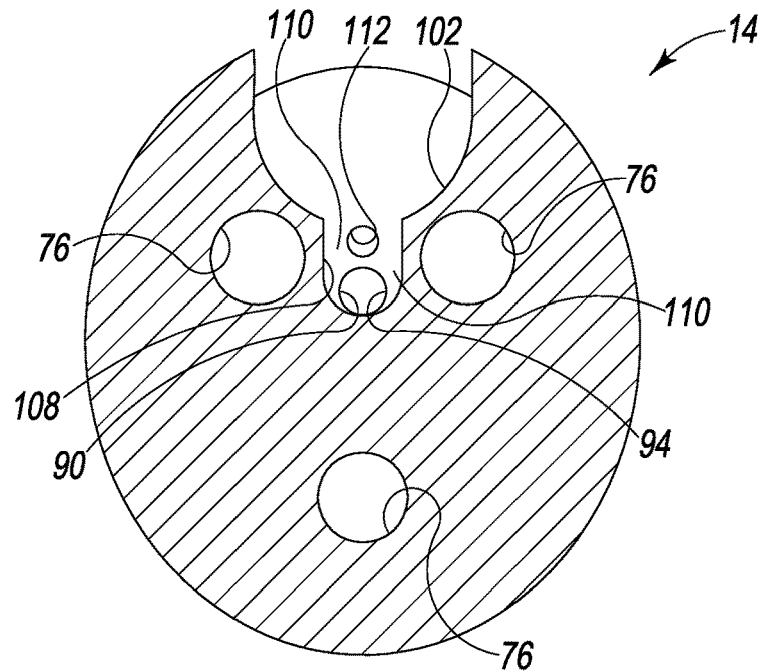
FIG. 6 is a cross section view of the patella drill guide and trial instrument taken along the line 6-6 of FIG. 7, as viewed in the direction of the arrows.

As alluded to above, the patella drill guide and trial instrument 14 may be selectively secured to the removable patella clamp 12. In that regard, the patella drill guide and trial instrument 14 includes a female connector geometry configured to receive the male geometry of the connector 32 of the patella clamp 12 (see FIG. 10). Specifically, the body of the patella drill guide and trial instrument 14 has a connecting slot 102 formed therein. As can be seen in FIGS. 7 and 8, the connecting slot 102 is positioned between the posterior trial bearing surface 52 and the anterior surface 62. The connecting slot 102 is shaped and sized to receive a connecting tongue 104 of the patella clamp's connector 32. As can be seen in FIGS. 10 and 11, the connecting tongue 104 includes a tip 106 which extends outwardly from a rounded surface of the main body of the connector 32. As can be seen in FIG. 6, the connecting slot 102 of the patella drill guide and trial instrument 14 has a similar shape, including a tip recess 108 that is sized and shaped to receive the tip 106 of the patella clamp's connecting tongue 104.

As can be seen in FIGS. 6 and 8, the upper sidewall 110 that defines the upper surface of the connecting slot 102 has a locking recess 112 defined therein. In the exemplary embodiment described herein, the locking recess 112 is generally hemispherical in shape. The locking recess 112 is sized and positioned to receive a locking mechanism of the patella clamp's connector 32 to secure the patella clamp 12 to the patella drill guide and trial instrument 14. In an embodiment, the locking mechanism is embodied as a biased plunger positioned on the tip 106 of the patella clamp's connecting tongue 104. In a specific embodiment, the biased plunger may be embodied as a spring-biased ball plunger 114. As the patella clamp's connector 32 is inserted in the connecting slot, the ball plunger 114 is urged downwardly against its spring bias by the upper sidewall 110 until it reaches a position in which the ball plunger 114 is moved into the locking recess 112 by its spring bias. When the ball plunger 114 is positioned in the locking recess 112, the patella clamp 12 is firmly secured to the patella drill guide and trial instrument 14 until sufficient force is applied to pull the two components apart by urging the ball plunger 114 downwardly out of the locking recess 112 to allow the patella clamp 12 to be separated from the patella drill guide and trial instrument 14.

As can be seen in FIG. 6, the alignment bore 90 of the patella drill guide and trial instrument 14 passes through the tip recess 108 of the connecting slot 102. As noted above, when the patella clamp 12 is secured to the patella drill guide and trial instrument 14, the tip 106 of the patella clamp's connecting tongue 104 is positioned in the tip recess 108 of the connecting slot 102. As shown in FIG. 11, when so positioned, the tip 106 of the patella clamp's connecting tongue 104 blocks the alignment bore 90 or otherwise prevents passage through it. More specifically, when the tip 106 of the patella clamp's connecting tongue 104 is positioned in the tip recess 108, a drill bit or other instrument is prevented from passing through the alignment bore 90.

In order to fit the needs of a given patient's anatomy, the patella drill guide and trial instrument 14 may be provided in a number of different sizes. For example, in the illustrative embodiment described herein, the patella drill guide and trial instrument 14 may be embodied in five different medial/lateral lengths (e.g., 29 mm, 32 mm, 35 mm, 38 mm, and 41 mm) so as to mimic the various sizes of the prosthetic patella components 18.

In the exemplary embodiment described herein, the patella drill guide and trial instrument 14 is embodied as a monolithic metal body constructed with a biocompatible metal that allows for smooth articulation between the patella drill guide and trial instrument 14 and the femoral component 154. Examples of such biocompatible metals include stainless steel, cobalt chrome, or titanium, although other metals or alloys may be used. The patella drill guide and trial instrument 14 may also be embodied as a monolithic polymer trial instrument. As such, the patella drill guide and trial instrument 14 may be made of any suitable medical-grade polymeric material. Examples of such polymeric materials include polyetheretherketone (PEEK), ultrahigh molecular weight polyethylene (UHMWPE), or acetal. In such an embodiment, the monolithic polymer trial may include metallic inserts (e.g., sleeves) positioned in the drill guide holes 76.

Figure 13:
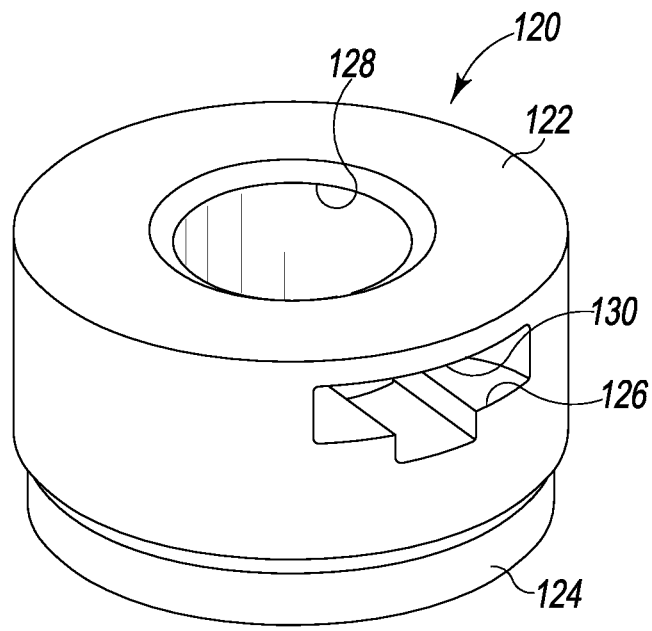
FIG. 13 is a perspective view of the compression socket.
Figure 14:
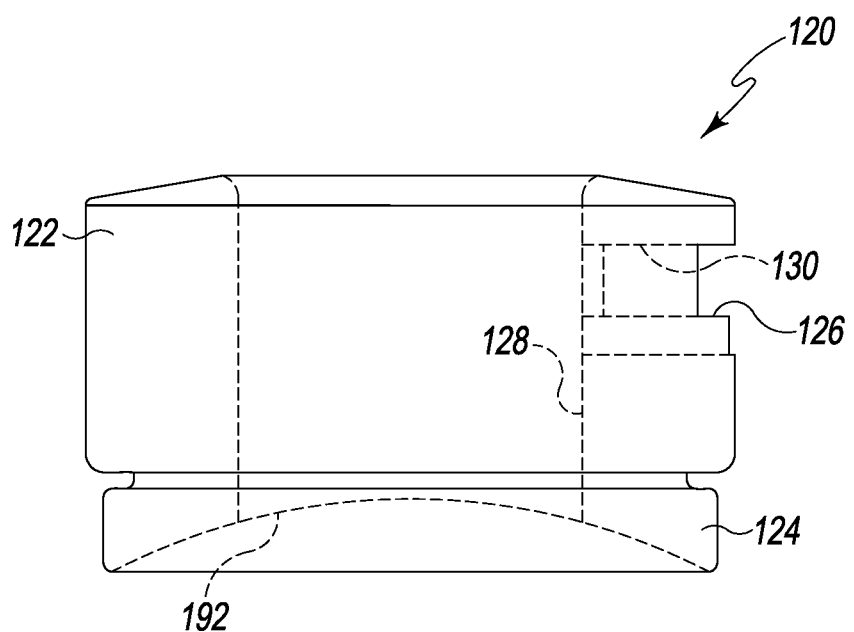
FIG. 14 is a side elevation view of the compression socket.

As can be seen in FIGS. 12-14, the removable clamp 12 may also be secured to a compression socket 120. The compression socket 120 may be used to assert clamping pressure on the patella component 18 as it is cemented in place on the patient's resected patella 16. The compression socket 120 includes a base in the form of a ring 122. The ring 122 has a ring-shaped compressible cushion 124 secured thereto. The compression cushion 124 is constructed of a deformable material and functions to engage the posterior bearing surface 188 of the patella component 18 thereby urging it toward the patella 16 when a clamping force is applied by use of the patella clamp 12.

The compression socket 120 includes a female connector geometry that is similar to that of the patella drill guide and trial instrument 14 and, as a result, configured to receive the male geometry of the connector 32 of the patella clamp 12 (see FIG. 12). Specifically, the ring 122 of the compression socket 120 has a connecting slot 126 formed therein. As can be seen in FIGS. 13 and 14, the connecting slot 126 is shaped and sized to receive the connecting tongue 104 of the patella clamp's connector 32. As can be seen in FIG. 12, the tip 106 of the connecting tongue 104 extends beyond the inner annular-shaped wall 128 of the compression socket's ring 122 such that the spring-biased ball plunger 114 engages the annular wall 128 of the ring 122 to secure clamp 12 to the compression socket 120. In particular, as the patella clamp's connector 32 is inserted into and through the compression socket's connecting slot 126, the ball plunger 114 is urged downwardly against its spring bias by the upper sidewall 130 until it exits the connecting slot 126 into the ring's center at which time the ball plunger 114 is moved upwardly by its spring bias. When the ball plunger 114 is so positioned, the patella clamp 12 is firmly secured to the compression socket 120 until sufficient force is applied to pull the two components apart by urging the ball plunger 114 downwardly and back into the connecting slot 126 thereby allowing the patella clamp 12 to be separated from the compression socket 120.

The ring 122 of the compression socket 120 may be embodied as a monolithic metal body constructed with a biocompatible such as stainless steel, cobalt chrome, or titanium, although other metals or alloys may be used. The ring 122 may also be embodied as a monolithic polymer trial instrument constructed with any suitable medical-grade polymeric material such as polyetheretherketone (PEEK), ultrahigh molecular weight polyethylene (UHMWPE), or acetal. The compressible cushion 124 may be constructed with any suitable medical-grade compressible material such as silicone.

Figure 15:
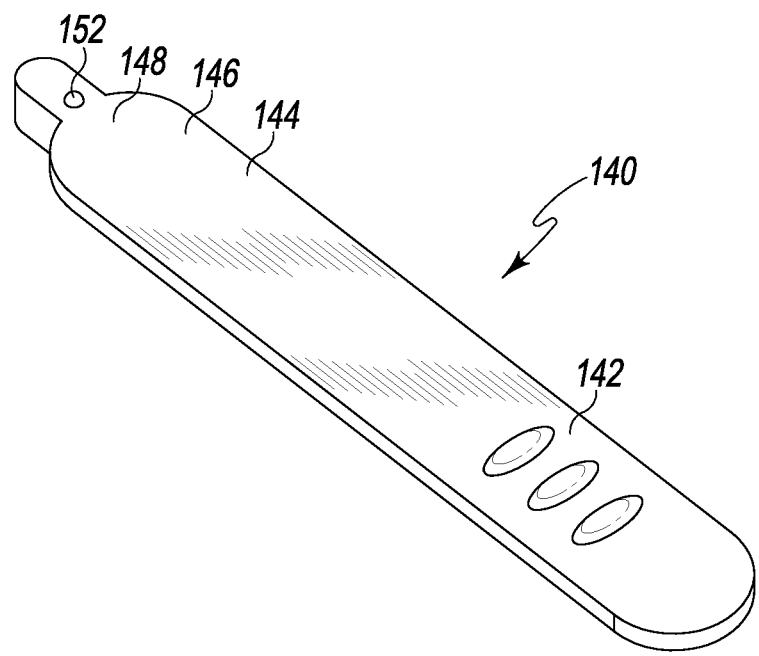
FIG. 15 is a perspective view of the alignment handle.
Figure 16:
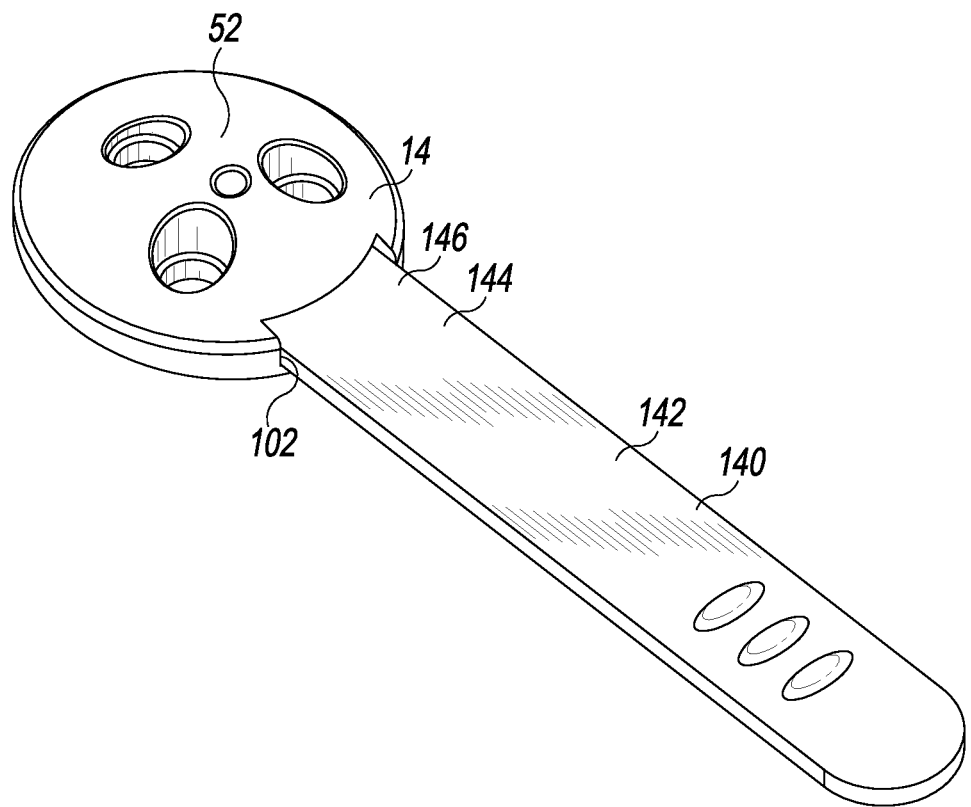
FIG. 16 is a perspective view showing the alignment handle secured to the patella drill guide and trial instrument.

As can be seen in FIGS. 15 and 16, the patella drill guide and trial instrument 14 may also be secured to an alignment handle 140. Use of the alignment handle 140 allows the surgeon to assess the rotational alignment of the patella drill guide and trial instrument 14 as it articulates in the trochlear groove of the femoral component 154 during trialing of the patellofemoral joint. The alignment handle 140 includes a relatively flat elongated flange 142 having a connector 144 formed in one end thereof. The connector 144 of the alignment handle is identical to the patella clamp's connector 32 so as to mate with the connector of the patella drill guide and trial instrument 14 in an identical manner as the patella clamp 12. As such, the alignment handle's connector 144 has a connecting tongue 146 that includes a tip 148 which extends outwardly from a rounded surface of the main body of the connector 144. The connecting tongue 146 and its tip 148 are received into the connecting slot 102 of the patella drill guide and trial instrument 14 in a similar manner as the similar structures of the patella clamp's connector 32.

Likewise, the alignment handle's connector 144 includes a locking mechanism to secure the alignment handle 140 to the patella drill guide and trial instrument 14. In an embodiment, the locking mechanism is embodied as a biased plunger positioned on the tip 148 of the alignment handle's connector 144. In a specific embodiment, the biased plunger may be embodied as a spring-biased ball plunger 152. The ball plunger 152 may be captured in the locking recess 112 of the connecting slot 102 of the patella drill guide and trial instrument 14 to firmly secure the alignment handle 140 to the patella drill guide and trial instrument 14 in an identical manner to as described above in regard to attachment of the patella clamp 12. The alignment handle 140 remains secured to the patella drill guide and trial instrument 14 by the ball plunger 152 until sufficient force is applied to pull the two components apart by urging the ball plunger 152 downwardly out of the locking recess 112 to allow the alignment handle 140 to be separated from the patella drill guide and trial instrument 14.

Figure 17:
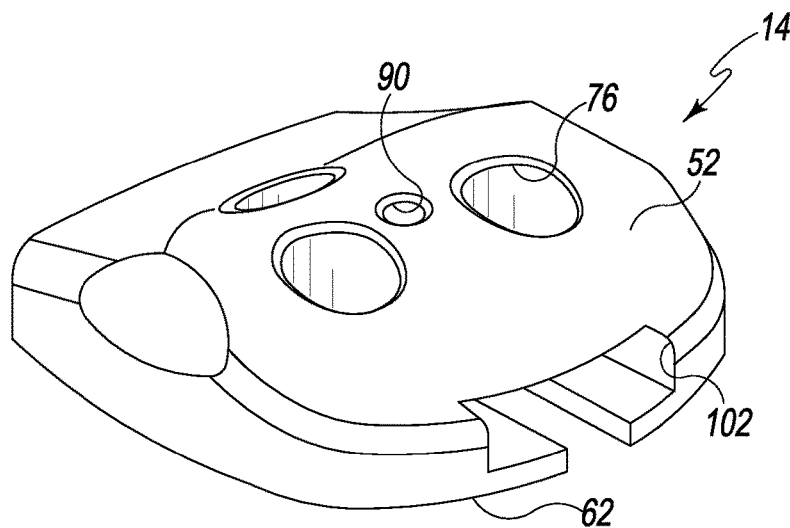
FIG. 17 is a view similar to FIG. 1, but showing an anatomic patella drill guide and trial instrument.

Referring now to FIG. 17, there is shown another embodiment of the patella drill guide and trial instrument 14. In particular, whereas the patella drill guide and trial instrument 14 of FIGS. 1-9 is embodied as a trial instrument mimicking a modified dome patella component, the patella drill guide and trial instrument 14 may be embodied to mimic other types of patella components. For example, as shown in FIG. 17, the patella drill guide and trial instrument 14 may be embodied to mimic "conforming" or "anatomic" patella components which are designed to conform with the condylar surfaces of the femur. Whereas modified dome patella components allow for greater movement between the patella component and the femoral component of the knee prosthesis, anatomic patella components are more constrained relative to the femoral component. As shown in FIG. 17, such an "anatomic" patella drill guide and trial instrument 14 may be embodied with similar features to as described above in regard to the "modified dome" patella drill guide and trial instrument 14.

Figure 19:
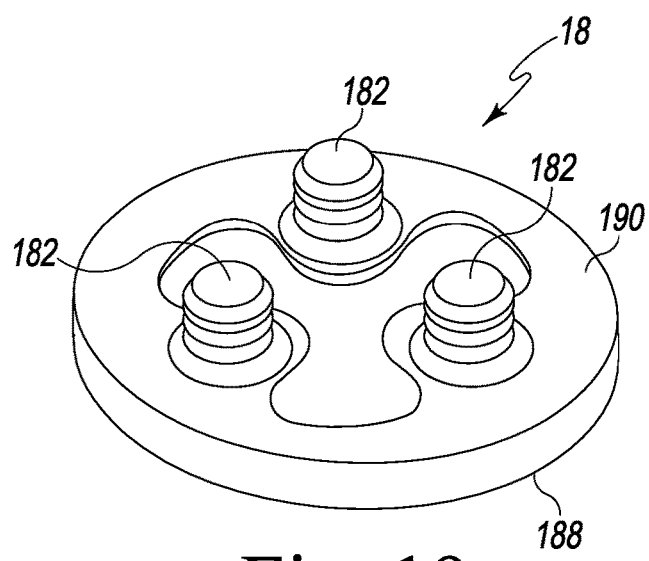
FIG. 19 is a bottom perspective view of the modified dome patella component of FIG. 18.
Figure 21:
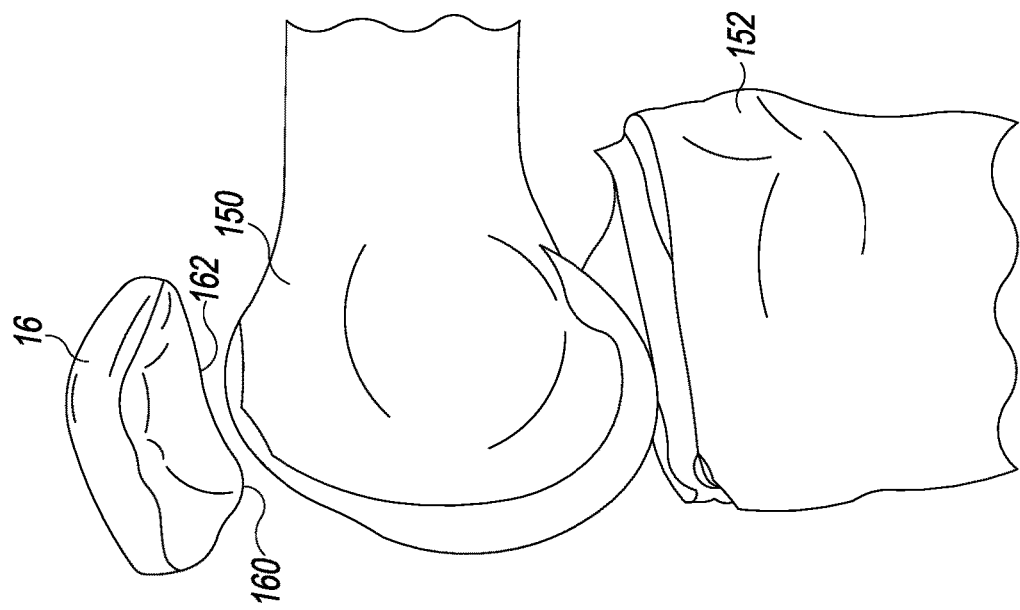
FIG. 21 is a lateral view of the knee of a patient.
Figure 20:
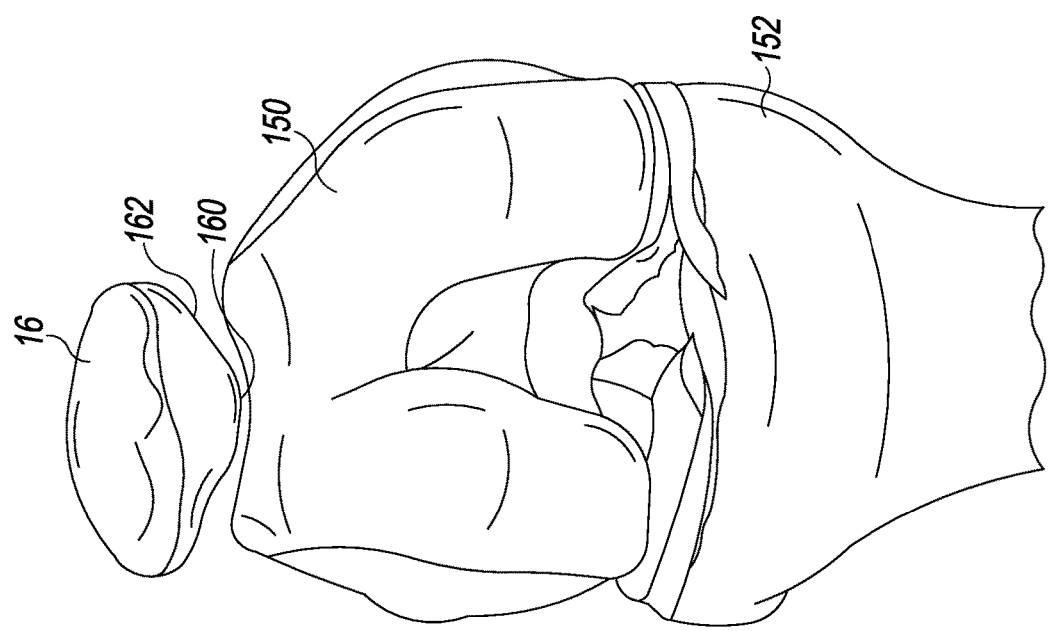
FIG. 20 is an anterior view of the knee of a patient.

Referring now to FIGS. 20-32, there is shown a surgical procedure in which the various instruments described herein in regard to FIGS. 1-17 are used to surgically prepare the patient's patella 16 for implantation of the prosthetic patella component 18 of FIGS. 19 and 20. The surgical procedure begins with preoperative planning in which, amongst other things, a CT scan or other type of preoperative image may be obtained to plan the placement location and orientation of the patella component 18. With the preoperative planning complete, the patient's soft tissue is dissected and retracted in order to allow access to the knee. Full exposure of the patient's joint is typically achieved so as to expose, in addition to the patella 16, the patient's femur 150 and tibia 152 (see FIGS. 20 and 21).

In addition to implantation of the patella component 18, the surgical procedure also replaces the patient's natural distal femur 150 with a prosthetic femoral component 154 and the patient's natural proximal tibia 152 with a tibial tray 156 and tibial bearing 158 (see FIGS. 28 and 29). However, the surgical implantation of the femoral component 154, the tibial tray 156, and tibial bearing 158 is not described in detail herein. Moreover, although the patella 16 is shown in its anatomical position relative to the femur 150 and the tibia 152 in FIGS. 20 and 21, the patella 16 is shown in isolation from its anatomical position in the remaining figures (with the exception of FIGS. 28 and 29) for clarity of description.

Figure 22:
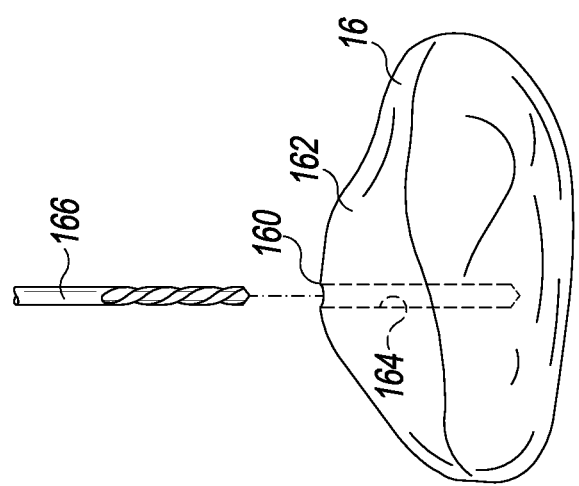
FIG. 22 is a surgical view showing an alignment hole being drilled into the apex of the patient's natural patella.

As shown in FIG. 22, prior to resection of the patient's patella 16, the surgeon first forms an alignment feature in the apex 160 of the patella's posterior surface 162. In particular, the surgeon may drill a hole 164 in the apex 160 of the posterior surface 162 of the patient's natural patella 16 with a drill 166 before resecting it. As can be seen in a comparison of FIGS. 22 and 23, the alignment hole 164 is drilled to a predetermined depth than is deeper than the thickness of the bone to be removed during patella resection. As such, the hole 164 (or a slight indentation depending on the depth of the drill) is still visible in the planar surgically-resected patellar surface 170 subsequent to bone removal.

Once the alignment hole 164 has been drilled in the posterior surface 162 of the patient's natural patella 16, the surgeon may then resect the patient's natural patella 16. Specifically, the surgeon may use a resection guide (not shown) and a bone saw (also not shown) to produce a generally planar surgically-resected patellar surface 170 onto which the patella component 18 will be subsequently implanted. Although numerous different instruments and methods may be used to resect the patient's natural patella 16, illustrative instruments and methods for doing so are described in commonly-owned, co-pending U.S. patent application Ser. No. 13/533,607 which is entitled "Patella Orthopaedic Surgical Method" and was filed on Jun. 26, 2012.

Figure 24:
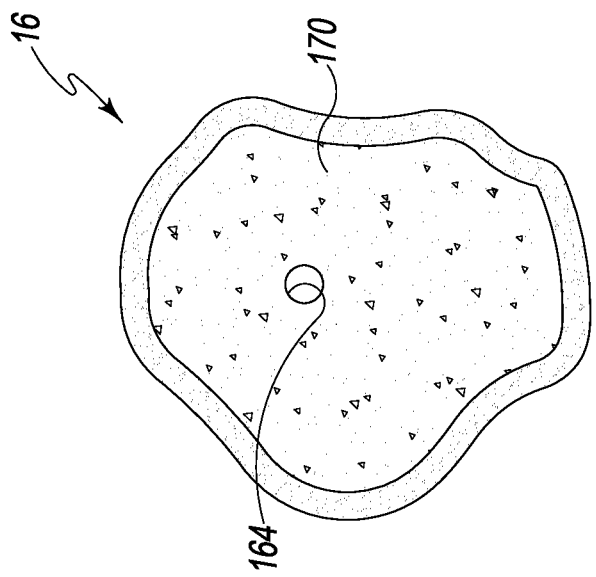
FIGS. 23 and 24 are surgical views showing the generally planar surgically-resected patella surface of the patient's patella.
Figure 23:
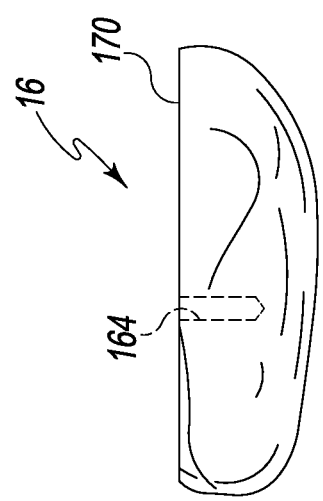

As alluded to above and as shown in FIGS. 23 and 24, the alignment hole 164 drilled by the surgeon prior to resection is still visible in the planar surgically-resected patellar surface 170 subsequent to bone removal. Depending on the depth of the drill procedure utilized to form the alignment hole 164, it may appear as a slight indentation in the surgically-resected patellar surface 170.

Figure 26:
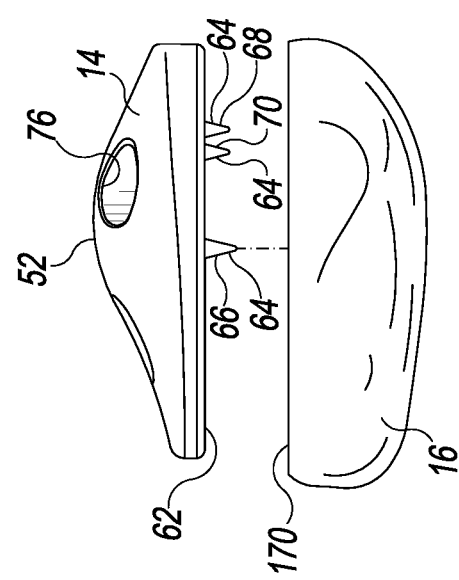
FIG. 26 is a surgical view showing the patella drill guide and trial instrument 14 being installed on the surgically-resected patella surface of the patient's patella.
Figure 25:
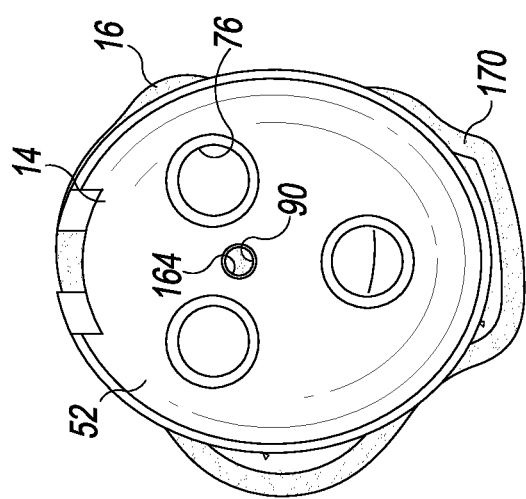
FIG. 25 is a surgical view showing alignment of the patella drill guide and trial instrument 14 over the surgically-resected patella surface of the patient's patella.

Once the resection of the patient's natural patella 16 is completed, the surgeon determines the appropriate size patella component 18 to implant on the surgically-resected patellar surface 170. To do so, the surgeon uses the patella drill guide and trial instrument 14. Specifically, as will now be described in more detail, the patella drill guide and trial instrument 14 may be secured to the patient's surgically-resected patellar surface 170 to function as both a sizing trial and a drill guide. To do so, the surgeon selects an initial one of the differently-sized patella drill guide and trial instruments 14 that the surgeon estimates is the proper size for the patient. As shown in FIGS. 25 and 26, the surgeon then positions the selected patella drill guide and trial instrument 14 over the surgically-resected patellar surface 170 and assesses coverage. Specifically, the surgeon first aligns the alignment bore 90 of the selected patella drill guide and trial instrument 14 with the alignment hole 164 drilled by the surgeon (prior to resection) in the planar surgically-resected patellar surface 170. To do so, the surgeon visualizes the drilled alignment hole 164 of the planar surgically-resected patellar surface 170 through the instrument's alignment bore 90 and adjusts the position of the selected patella drill guide and trial instrument 14 such that the drilled alignment hole 164 and the instrument's alignment bore 90 are aligned with one another. Once aligned in such a manner, the surgeon may then assess the coverage of the selected patella drill guide and trial instrument 14. If the surgeon determines the selected patella drill guide and trial instrument 14 is not the proper size, the initial patella drill guide and trial instrument 14 is removed and a patella drill guide and trial instrument 14 having a different size is selected, aligned over the surgically-resected patellar surface 170, and assessed.

Once the patella drill guide and trial instrument 14 of the proper size has been determined, the surgeon secures the patella drill guide and trial instrument 14 to the surgically-resected patellar surface 170. To do so, the surgeon positions the patella drill guide and trial instrument 14 in a desired location and orientation for the final implant (i.e., the patella component 18) by aligning the alignment bore 90 of the selected patella drill guide and trial instrument 14 with the drilled alignment hole 164 of the planar surgically-resected patellar surface 170. So positioned, the spikes 64 of the patella drill guide and trial instrument 14 face downwardly toward the surgically-resected patellar surface 170. As can be seen in FIG. 26, when aligned over the surgically-resected patellar surface 170, the peripheral spikes 68, 70 of the patella drill guide and trial instrument 14 are medially positioned relative to the center of the patella 16.

As can also be seen in FIG. 26, as the patella drill guide and trial instrument 14 is urged toward the patella 16, the center spike 66, which is longer than both the peripheral spikes 68, 70, is first to contact the surgically-resected patellar surface 170. In such a way, rotational positioning of the patella drill guide and trial instrument 14 can be achieve prior to securing it in its final position on the surgically-resected patellar surface 170. In particular, the surgeon may first insert the tip of the center spike 66 into the surgically-resected patellar surface 170 of the patient's patella 16. The surgeon may then adjust the rotational position of the patella drill guide and trial instrument 14 by rotating it relative to the surgically-resected patellar surface 170 about its central axis defined by the center spike 66.

Figure 27:
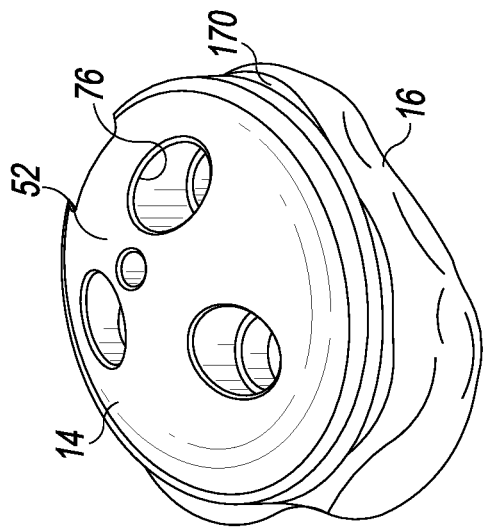
FIG. 27 is a surgical view showing the patella drill guide and trial instrument 14 having been installed on the surgically-resected patella surface of the patient's patella.

As shown in FIG. 27, once the patella drill guide and trial instrument 14 has been rotated into a desired alignment position, the patella drill guide and trial instrument 14 may be pressed into the surgically-resected patellar surface 170 such that the peripheral spikes 68, 70 engage and seat in the bone tissue of the surgically-resected patellar surface 170. Doing so prevents further rotation of the patella drill guide and trial instrument 14 and maintains it in its desired position relative to the surgically-resected patellar surface 170 of the patient's patella 16.

It should be appreciated that the surgeon may press the patella drill guide and trial instrument 14 into the bone tissue of the surgically-resected patellar surface 170 by hand with the application of finger pressure alone. However, in certain cases, it may be necessary to utilize additional force in order to fully seat the patella drill guide and trial instrument 14 in the surgically-resected patellar surface 170. In such cases, the surgeon may install the removable clamp 12 to the patella drill guide and trial instrument 14 and use the clamp 12 to apply a clamping force which urges the instrument's spikes 64 into the bone tissue of the surgically-resected patellar surface 170 so as to fully seat the patella drill guide and trial instrument 14.

Once the patella drill guide and trial instrument 14 has been installed on the surgically-resected patellar surface 170, the surgeon may then perform a trial of the patellofemoral joint to assess size and positioning. To do so, the surgeon first installs the alignment handle 140 to the patella drill guide and trial instrument 14. Use of the alignment handle 140 allows the surgeon to assess the rotational alignment of the patella drill guide and trial instrument 14 as it articulates in the trochlear groove of the femoral component 154 during trialing of the patellofemoral joint. To secure the alignment handle 140 to the patella drill guide and trial instrument 14, the surgeon inserts the handle's connector 144 into the connecting slot 102 of the patella drill guide and trial instrument 14. In doing so, the handle's ball plunger 152 is captured in the locking recess 112 of the connecting slot 102 of the patella drill guide and trial instrument 14 to firmly secure the alignment handle 140 to the patella drill guide and trial instrument 14.

Once the alignment handle 140 is installed, the surgeon may then position the patella drill guide and trial instrument 14 such that its posterior trial bearing surface 52 is positioned to articulate within the trochlear groove 176 of the femoral condyle surfaces 172, 176 of the femoral component 154. The surgeon may then manipulate the patient's leg so as to perform a trial articulation of the patellofemoral joint. In doing so, the surgeon may use the alignment handle 140 as a visual indicator of the rotational alignment of the patella drill guide and trial instrument 14 as it articulates in the trochlear groove 176 of the femoral component 154. Specifically, as can be seen in FIG. 28, if the medial edge of the patella drill guide and trial instrument 14 (i.e., the edge into which the connecting slot 102 is formed) is properly aligned, the alignment handle 140 extends outwardly in a direction generally perpendicular to the long axis of the femur and tibia. That is, it extends outwardly generally in the medial/lateral direction.

However, if the rotational position of the patella drill guide and trial instrument 14 is not properly aligned, the alignment handle extends outwardly at an angle which is skewed, such as shown in FIG. 29. That is, if not properly aligned, the alignment handle 140 extends outwardly in a direction that is not generally perpendicular to the long axis of the femur and tibia. As such, the alignment handle 140 is not arranged generally in the medial/lateral direction.

Based on the above, the surgeon may assess the rotational position and alignment of the patella drill guide and trial instrument 14 throughout a trial articulation of the patellofemoral joint by monitoring the position of the alignment handle 140. If at any time during the trialing procedure the alignment handle 140 does not maintain the desired angle relative to the long axis of the femur and tibia (i.e., it does not extend generally in the medial/lateral direction), the surgeon may perform a corrective procedure on the positioning of the patella drill guide and trial instrument 14 to improve the rotational positioning thereof.

Once the surgeon has completed the trial articulation of the patellofemoral joint and made any necessary adjustments to the position of the patella drill guide and trial instrument 14, the surgeon may then drill a number of anchor holes 180 in the surgically-resected patellar surface 170. The anchor holes 180 are sized and positioned to receive the anchor pegs 182 of the patella component 18 (see FIG. 19). To do so, the surgeon first secures the removable clamp 12 to the patella drill guide and trial instrument 14 by advancing the clamp's connector 32 into the connecting slot 102 of the patella drill guide and trial instrument 14. In doing so, the handle's ball plunger 114 is captured in the locking recess 112 of the connecting slot 102 of the patella drill guide and trial instrument 14 to firmly secure the patella clamp 12 to the patella drill guide and trial instrument 14.

The surgeon then squeezes the clamp's handles 26, 30 toward one another, thereby moving the patella drill guide and trial instrument 14 and the retaining socket 28 toward one another so as to clamp the patella 16 therebetween. With the patella 16 secured by the clamp 12, the surgeon may now drill the anchor holes 180. To do so, the surgeon advances the rotating tip 184 of the surgical drill's bit 84 into the opening formed in the posterior trial bearing surface 52 of one of the drill guide holes 76 and through the patella drill guide and trial instrument 14 so that it exits the guide hole 76 through the instrument's anterior surface 62 and enters the bone tissue of the surgically-resected patellar surface 170. The surgeon continues to advance the drill bit 84 into the patella 16 until the lower surface of the bit's collar 86 bottoms out or otherwise engages the depth stop (i.e., the shoulder 82) of the counterbored guide hole 76. The surgeon then drills the remaining anchor holes 180 in a similar manner.

Figure 31:
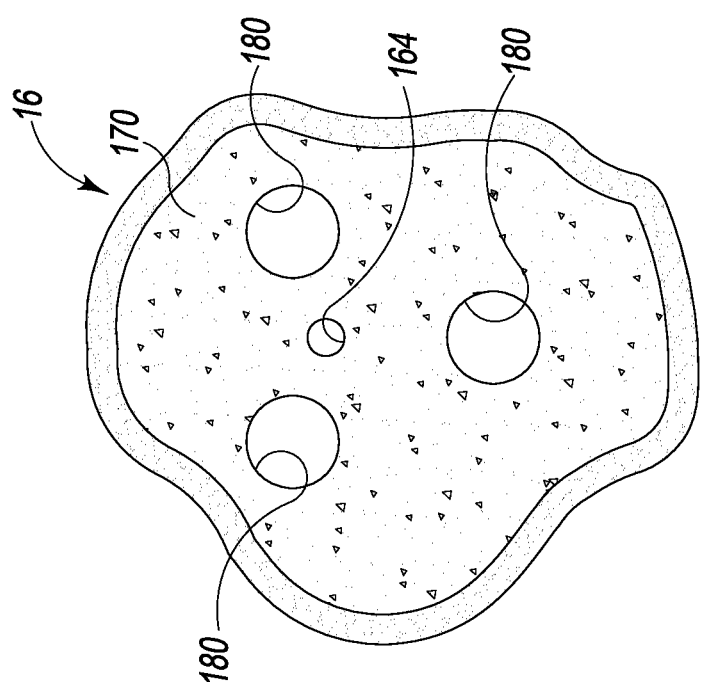
FIG. 31 is a view similar to FIG. 24, but showing the anchor holes having been drilled in the patient's patella.

As noted above, the size and position of each of the drill guide holes 76 coincides with the size and position of the anchor pegs 182 of the patella component 18 (see FIG. 19). As such, once the surgeon has advanced the drill's surgical bit 84 through each of the guide holes 76, the surgically-resected patellar surface 170 is prepared for implantation of the patella component 18, as shown in FIG. 31.

It should be appreciated that during such drilling of the anchor holes 180, the surgeon is prevented from advancing the drill's surgical bit 84 through the alignment bore 90 of the patella drill guide and trial instrument 14 since the bore's diameter is smaller than the bit's diameter. Moreover, as described above, when the patella clamp 12 is secured to the patella drill guide and trial instrument 14, the tip 106 of the patella clamp's connecting tongue 104 is positioned in the tip recess 108 of the instrument's connecting slot 102. As shown in FIG. 11, when so positioned, the tip 106 of the patella clamp's connecting tongue 104 blocks the alignment bore 90 or otherwise prevents passage through it. As such, not only is the drill bit 84 used for drilling the anchor holes 180 prevented from advancing through the alignment bore 90 due to the bore's smaller diameter, other instruments are likewise prevented from passing through the alignment bore 90 to the surgically-resected patellar surface 170 by the presence of the tip 106 of the patella clamp's connecting tongue 104 being positioned in the tip recess 108 of the instrument's connecting slot 102.

It should also be appreciated that in some cases, the surgeon may desire to utilize the patella drill guide and trial instrument 14 to drill the anchor holes 180 without using the patella clamp 12. In such a case, the surgeon may maintain the patella drill guide and trial instrument 14 with the application of finger pressure alone.

Figure 32:
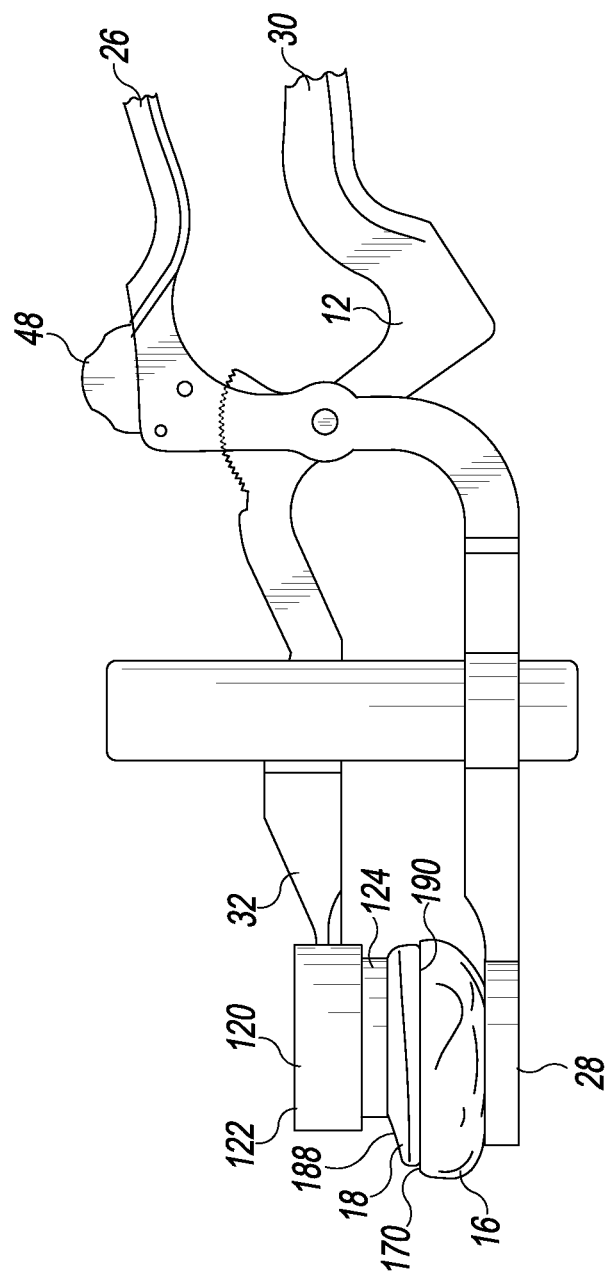
FIG. 32 shows the patella clamp and compression socket being used to clamp the patella component to the patient's patella during the bone cement polymerization process.

Referring now to FIG. 32, once the anchor holes 180 have been drilled in the surgically-resected patellar surface 170, the surgeon implants the appropriately sized patella component 18 (i.e., a component 18 having a size (i.e., medial/lateral length) selected through trialing as described above) in the patient's patella 16. The surgeon may first apply bone cement to the anterior surface 190 of the patella component 18. The patella component 16 is then positioned over the surgically-resected patellar surface 170 such that the component's anchor pegs 182 are aligned with their respective anchor holes 180. Thereafter, the patella component 12 may be advanced such that the anchor pegs 182 are received into the anchor holes 180 and the anterior surface 190 is positioned in contact with the surgically-resected patellar surface 170.

The removable clamp 12 may then be secured to the compression socket 120 by inserting the clamp's connector 32 into the socket's connecting slot 126. The compression socket 120 may then be used to assert clamping pressure on the patella component 18 as it is cemented in place on the patient's resected patella 16. That is, the compression socket 120 and clamp 12 may be used to maintain clamping pressure on the patella component 18 as the bone cement polymerizes. To do so, the ring-shaped compressible cushion 124 of the compression socket 120 is positioned over the posterior bearing surface 188 of the patella component 18. The surgeon then squeezes the clamp's handles 26, 30 toward one another, thereby moving the compression socket 120 and the retaining socket 28 toward one another. During such movement, the compressible cushion 120 of the compression socket 120 is advanced into contact with the posterior bearing surface 188 of the patella component 16. The patella component 16 is seated within and stabilized by a concave surface 192 of the compressible cushion 120 (see FIG. 14) such that the patella component 16 is clamped firmly to the resected patella 16 until polymerization is complete and the patella component 16 is secured thereto. The surgeon may slide the patella clamp's button 48 forward to lock the clamp 12 in its current position during the polymerization process.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. A method of performing an orthopaedic surgical procedure on a patella of a patient, comprising:
   forming a hole in the apex of the patella of the patient without the use of a cutting guide,
   resecting the patella of the patient to produce a generally planar resected patellar surface after the hole is formed in the apex of the patella of the patient, and
   positioning a drill guide, having an alignment bore formed therein, on the resected patellar surface such that the alignment bore of the drill guide is aligned with a portion of the hole formed in the patella of the patient.

2. The method of claim 1, further comprising identifying the apex of a posterior surface of a patient's natural patella.

3. The method of claim 1, further comprising advancing a drill through a number of guide holes formed in the drill guide and into the resected patellar surface to form a number of anchor holes in the patella of the patient.

4. The method of claim 3, further comprising:
   removing the drill guide from the resected patellar surface, and
   inserting a number of anchor pegs of a patella component into the anchor holes.

5. The method of claim 3, wherein advancing the drill through the number of guide holes formed in the drill guide comprises:
   advancing a drill bit into each guide hole of the number of guide holes until an annular collar of the drill bit abuts a shoulder formed in the guide hole.

6. The method of claim 3, wherein the alignment bore has a different diameter than each of the number of guide holes.

7. The method of claim 3, wherein the alignment bore has a smaller diameter than each of the number of guide holes.

8. The method of claim 1, wherein positioning the drill guide on the resected patellar surface comprises:
   visualizing the hole formed in the patella of the patient through the alignment bore, and
   aligning the drill guide such that the alignment bore aligns with the hole formed in the patella of the patient.

9. The method of claim 1, wherein:
   forming the hole in the patella of the patient comprises drilling a hole in the patella of the patient to a predetermined depth, and
   resecting the patella of the patient comprises resecting a thickness of patellar bone that is less than the predetermined depth such that the drilled hole is visible on the resected patellar surface.

10. The method of claim 1, further comprising:
    trialing the patellofemoral joint with the drill guide positioned on the patella of the patient, and
    advancing a drill through a number of guide holes formed in the drill guide and into the resected patellar surface so as to drill a number of anchor holes in the patella of the patient subsequent to trialing the patellofemoral joint.

* * * * *